United States Patent
Barsanti et al.

(10) Patent No.: US 8,748,626 B2
(45) Date of Patent: Jun. 10, 2014

(54) OXAZOLE AND THIAZOLE COMPOUNDS AS KSP INHIBITORS

(75) Inventors: Paul A. Barsanti, Pleasant Hill, CA (US); Yu Ding, Union City, CA (US); Wooseok Han, San Ramon, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/640,561

(22) PCT Filed: Apr. 13, 2011

(86) PCT No.: PCT/EP2011/055855
§ 371 (c)(1),
(2), (4) Date: Dec. 5, 2012

(87) PCT Pub. No.: WO2011/128388
PCT Pub. Date: Oct. 20, 2011

(65) Prior Publication Data
US 2013/0224186 A1  Aug. 29, 2013

Related U.S. Application Data

(60) Provisional application No. 61/324,678, filed on Apr. 15, 2010.

(51) Int. Cl.
| | | |
|---|---|---|
| *A61K 31/422* | (2006.01) | |
| *A61K 31/427* | (2006.01) | |
| *C07D 277/28* | (2006.01) | |
| *C07D 277/30* | (2006.01) | |
| *C07D 263/32* | (2006.01) | |
| *C07D 413/12* | (2006.01) | |
| *C07D 417/12* | (2006.01) | |
| *C07D 417/14* | (2006.01) | |

(52) U.S. Cl.
USPC ........... 548/181; 548/204; 548/236; 514/365; 514/374

(58) Field of Classification Search
USPC .......................................... 548/204, 236, 181
See application file for complete search history.

(56) References Cited

FOREIGN PATENT DOCUMENTS

| WO | WO 2006/002236 | 1/2006 |
| WO | WO 2008/063912 | 5/2008 |
| WO | WO 2009/077448 | 6/2009 |

OTHER PUBLICATIONS

Golub et al., Science, vol. 286, Oct. 15, 1999, pp. 531-537.*

* cited by examiner

*Primary Examiner* — Laura L. Stockton
(74) *Attorney, Agent, or Firm* — Stephen Johnson; Michael Smith

(57) ABSTRACT

Disclosed are new substituted oxazole and thiazole compounds of Formula (I) and pharmaceutically acceptable salts, esters or prodrugs thereof, compositions of the derivatives together with pharmaceutically acceptable carriers, and uses thereof:

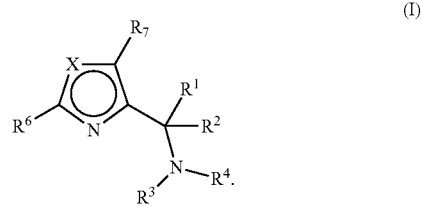

24 Claims, No Drawings

OXAZOLE AND THIAZOLE COMPOUNDS AS KSP INHIBITORS

CROSS-REFERENCE TO RELATED APPLICATIONS

This application is the U.S. National Stage of International Application No. PCT/EP2011/055855, filed 13 Apr. 2011, which claims the benefit of priority to U.S. Provisional Application Ser. No. 61/324,678, filed on Apr. 15, 2010, each of which is incorporated herein by reference in its entirety.

FIELD OF THE INVENTION

This invention generally relates to oxazole and thiazole compounds and pharmaceutically acceptable salts, esters, or prodrugs thereof. This invention is further directed to compositions of such compounds together with pharmaceutically acceptable carriers, to uses of such compounds, to their preparation, and to related intermediates.

STATE OF THE ART

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmic reticulum. Several KRPs interact with the microtubules of the mitotic spindle or with the chromosomes directly and appear to play a pivotal role during the mitotic stages of the cell cycle. These mitotic KRPs are of particular interest for the development of cancer therapeutics.

Kinesin spindle protein (KSP) (also known as Eg5, HsEg5, KNSL1, or KIF11) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., Cell 83:1159-1169, 1995). Mutations in bimC and cut7 genes, which are considered to be homologues of KSP, cause failure in centrosome separation in *Aspergillus nidulans* (Enos, A. P., and N. R. Morris, Cell 60:1019-1027, 1990) and *Schizosaccharomyces pombe* (Hagan, I., and M. Yanagida, Nature 347:563-566, 1990). Treatment of cells with either ATRA (all trans-retinoic acid), which reduces KSP expression on the protein level, or depletion of KSP using antisense oligonucleotides revealed a significant growth inhibition in DAN-G pancreatic carcinoma cells indicating that KSP might be involved in the antiproliferative action of all trans-retinoic acid (Kaiser, A., et al., J. Biol. Chem. 274, 18925-18931, 1999). Interestingly, the *Xenopus laevis* Aurora-related protein kinase pEg2 was shown to associate and phosphorylate XlEg5 (Giet, R., et al., J. Biol. Chem. 274:15005-15013, 1999). Potential substrates of Aurora-related kinases are of particular interest for cancer drug development. For example, Aurora 1 and 2 kinases are overexpressed on the protein and RNA level and the genes are amplified in colon cancer patients.

The first cell permeable small molecule inhibitor for KSP, "monastrol," was shown to arrest cells with monopolar spindles without affecting microtubule polymerization as do conventional chemotherapeutics such as taxanes and vinca alkaloids (Mayer, T. U., et al., Science 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., Biochemistry, 42:338-349, 2003; Kapoor, T. M., et al., J. Cell Biol., 150:975-988, 2000).

In light of the importance of improved chemotherapeutics, there is a need for KSP inhibitors that are effective in vivo inhibitors of KSP and KSP-related proteins.

SUMMARY OF THE INVENTION

In one embodiment, this invention is directed to substituted oxazole and thiazole compounds and the pharmaceutically acceptable salts, esters, or prodrugs thereof, their preparation, pharmaceutical compositions, and uses for treating KSP mediated diseases, wherein the compounds are represented by the Formula (I):

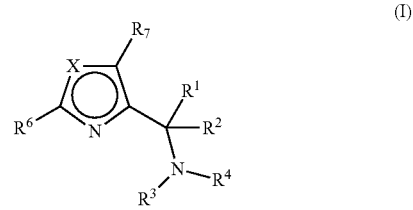

wherein:

$R^1$ is selected from the group consisting of alkyl, branched alkyl, and substituted alkyl;

$R^2$ is selected from the group consisting of hydrogen, alkyl, and substituted alkyl;

$R^3$ is selected from the group consisting of $-L^1-A^1$, wherein $L^1$ is selected from the group consisting of —C(O)—, —C(S)—, —S(O)—, and —S(O)$_2$— and $A^1$ is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, substituted heterocycloalkyl, and $NR^8R^9$;

$R^4$ is selected from the group consisting of hydrogen, alkyl, substituted alkyl, alkenyl, substituted alkenyl, alkynyl, and substituted alkynyl, and optionally substituted pyrrolidinyl;

or $R^3$ and $R^4$ together with the nitrogen atom bound thereto join to form a five to seven member heterocycloalkyl or substituted heterocycloalkyl group where optionally one carbon ring atom is selected from the group consisting of O, S, or $NR^{11}$;

X is O or S;

$R^6$ is selected from the group consisting of cycloalkyl, heterocycloalkyl, aryl, and heteroaryl, all of which may be optionally substituted with)-$(R^{10})_m$ where $R^{10}$ is as defined herein, m is 1, 2, 3, or 4, and each $R^{10}$ may be the same or different when m is 2, 3, or 4;

$R^7$ is $-L^2-A^2$ wherein $L^2$ is $C_1$-$C_5$ alkylene and $A^2$ is selected from the group consisting of aryl, substituted aryl, heteroaryl, substituted heteroaryl, cycloalkyl, substituted cycloalkyl, heterocycloalkyl, and substituted heterocycloalkyl, provided that $R^7$ is not attached to X;

$R^8$ is selected from the group consisting of hydrogen and alkyl;

$R^9$ is selected from the group consisting of hydrogen, hydroxy, alkyl, substituted alkyl, aryl, substituted aryl, heteroaryl, substituted heteroaryl, cycloalkyl, substituted cycloalkyl, heterocycloalkyl, and substituted heterocycloalkyl;

or $R^5$ and $R^9$ together with the nitrogen atom pendent thereto join to form a heterocycloalkyl or substituted heterocycloalkyl;

$R^{10}$ is selected from the group consisting of cyano, alkyl, substituted alkyl, alkenyl, substituted alkenyl, alkynyl, substituted alkynyl, —$CF_3$, alkoxy, substituted alkoxy, halo, and hydroxy; and $R^{11}$ is selected from the group consisting of hydrogen, alkyl, substituted alkyl, —$SO_2$alkyl, and —$SO_2$ substituted alkyl.

DETAILED DESCRIPTION OF THE INVENTION

Compounds of the invention include those of Formula (I) or a pharmaceutically acceptable salt, ester, or prodrug thereof:

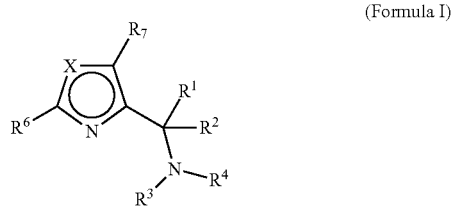

(Formula I)

wherein:

$R^1$ is selected from the group consisting of alkyl, branched alkyl, and substituted alkyl;

$R^2$ is selected from the group consisting of hydrogen, alkyl, and substituted alkyl;

$R^3$ is selected from the group consisting of -$L^1$-$A^1$, wherein L' is selected from the group consisting of —C(O)—, —C(S)—, —S(O)—, and —S(O)$_2$— and A' is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, substituted heterocycloalkyl, and $NR^8R^9$;

$R^4$ is selected from the group consisting of hydrogen, alkyl, substituted alkyl, alkenyl, substituted alkenyl, alkynyl, and substituted alkynyl, and optionally substituted pyrrolidinyl;

or $R^3$ and $R^4$ together with the nitrogen atom bound thereto join to form a five to seven member heterocycloalkyl or substituted heterocycloalkyl group where optionally one carbon ring atom is selected from the group consisting of O, S, or $NR^{11}$;

X is O or S;

$R^6$ is selected from the group consisting of cycloalkyl, heterocycloalkyl, aryl, and heteroaryl, all of which may be optionally substituted with —$(R^{10})_m$ where $R^{10}$ is as defined herein, m is 1, 2, 3, or 4, and each $R^{10}$ may be the same or different when m is 2, 3, or 4;

$R^7$ is -$L^2$-$A^2$ wherein $L^2$ is $C_1$-$C_5$ alkylene and $A^2$ is selected from the group consisting of aryl, substituted aryl, heteroaryl, substituted heteroaryl, cycloalkyl, substituted cycloalkyl, heterocycloalkyl, and substituted heterocloalkyl, provided that $R^7$ is not attached to X;

$R^8$ is selected from the group consisting of hydrogen and alkyl;

$R^9$ is selected from the group consisting of hydrogen, hydroxy, alkyl, substituted alkyl, aryl, substituted aryl, heteroaryl, substituted heteroaryl, cycloalkyl, substituted cycloalkyl, heterocycloalkyl, and substituted heterocycloalkyl;

or $R^8$ and $R^9$ together with the nitrogen atom pendent thereto join to form a heterocycloalkyl or substituted heterocycloalkyl;

$R^{10}$ is selected from the group consisting of cyano, alkyl, substituted alkyl, alkenyl, substituted alkenyl, alkynyl, substituted alkynyl, —$CF_3$, alkoxy, substituted alkoxy, halo, and hydroxy; and $R^{11}$ is selected from the group consisting of hydrogen, alkyl, substituted alkyl, —$SO_2$alkyl, and —$SO_2$ substituted alkyl.

A preferred embodiment provides a compound of Formula I, wherein $R^1$ is alkyl. Another preferred embodiment provides a compound of Formula I wherein, $R^2$ is $C_{1-4}$ alkyl or H, with H being further preferred. Yet another embodiment provides a compound of Formula I wherein, $R^1$ is i-propyl, or t-butyl. Provided in yet another embodiment is a compound of Formula I wherein, $R^3$ is selected from -$L^1$-$A^1$, wherein $L^1$ is selected from the group consisting of —C(O)—, —S(O)—, and —S(O)$_2$— and $A^1$ is selected from the group consisting of alkyl, substituted alkyl. A further preferred embodiment provides a compound of Formula I wherein, $R^3$ is selected from -$L^1$-$A^1$, wherein L' is —C(O)—, and $A^1$ is substituted alkyl.

Another embodiment of the present invention provides a compound of Formula I, wherein: wherein $R^4$ is selected from the group consisting of hydrogen, alkyl, and substituted alkyl, and preferably $R^4$ is substituted alkyl —$CH_2$-fluoropyrrolidinyl. Provided in another embodiment is a compound of Formula I, wherein $R^3$ is selected from -$L^1$-$A^1$, wherein $L^1$ is —C(O)—, and $A^1$ is —$CH(CH_3)OH$. Yet another embodiment provides a compound of Formula I, wherein $R^4$ is —$(CH_2)_2$—$CH(CH_2F)NH_2$, or —$CH_2$-3-fluoropyrrolidinyl. A further preferred embodiment provides a compound of Formula I wherein $R^6$ is selected from the group consisting of aryl, and heteroaryl, all of which are be optionally substituted with)-$(R^{10})_m$ where $R^{10}$ is as defined above, m is 1, 2, 3, or 4, and each $R^{10}$ may be the same or different when m is 2, 3, or 4; and $R^7$ is -$L^2$-$A^2$ wherein $L^2$ is $C_1$-$C_2$ alkylene and $A^2$ is selected from the group consisting of aryl, and heteroaryl. Preferably this embodiment provides a compound of Formula I, wherein $R^6$ represents aryl substituted with two $R^{10}$ groups, and it is further preferred when $R^6$ represents phenyl substituted with two fluorine atoms.

Yet another embodiment of the present invention provides a compound of Formula I, wherein $R^7$ represents —$CH_2$-aryl, preferably, $R^7$ represents —$CH_2$-phenyl, and $R^6$ represents 1,4-difluoro-phenyl. A particularly preferred compound of Formula I is selected from:

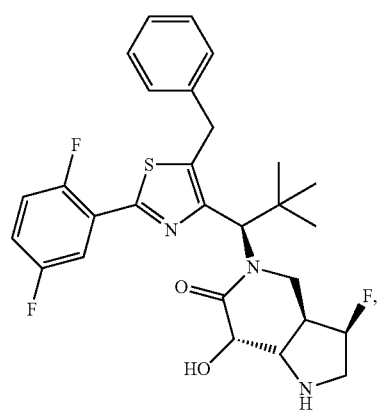
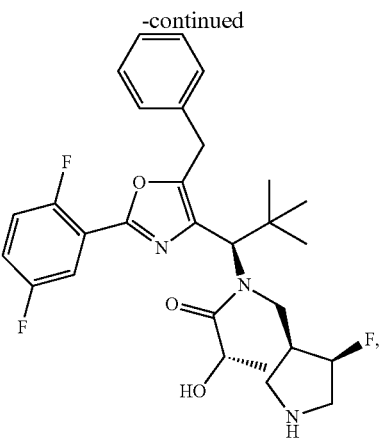
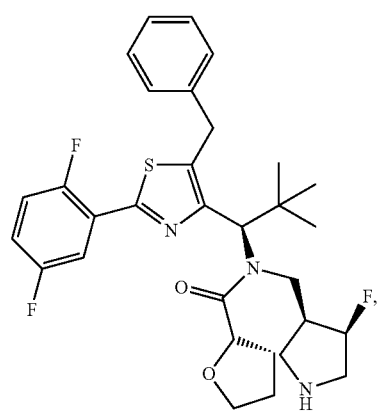
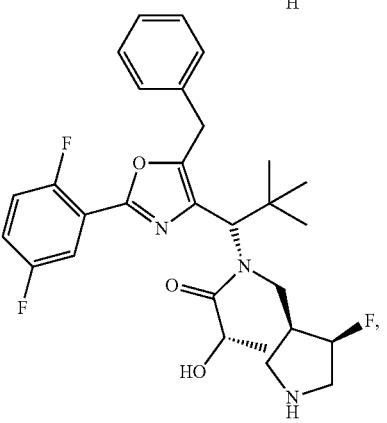
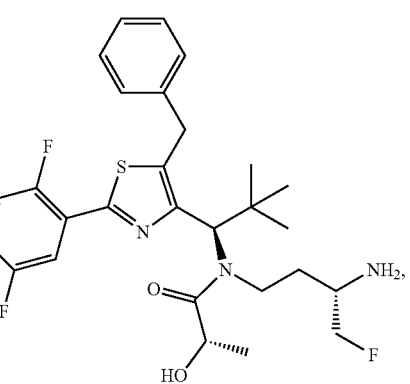
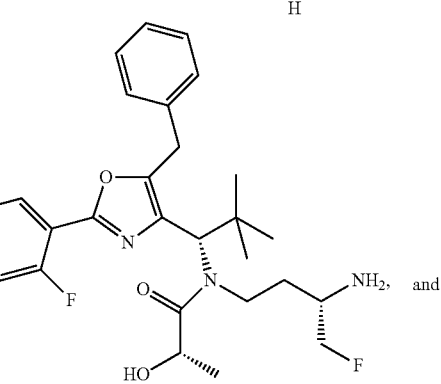
and
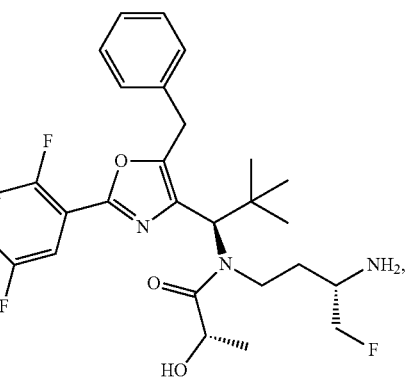
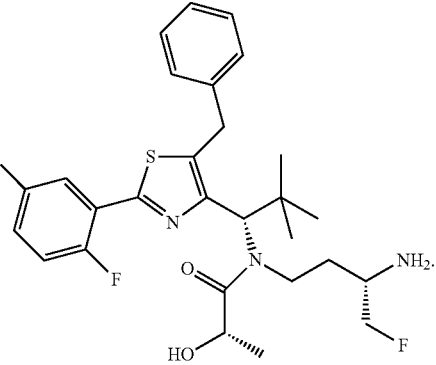
Another aspect of the present invention provides a pharmaceutical composition comprising a therapeutically effective amount of a compound of Formula I, and a pharmaceutically acceptable carrier. A preferred aspect of this embodiment provides a composition further comprising at least one additional agent for the treatment of cancer. It is preferred that the additional agent for the treatment of cancer be selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

Yet another aspect of the present invention provides a method of treating a disorder mediated, at least in part, by KSP in a mammalian patient comprising administering to a mammalian patient in need of such treatment a therapeutically effective amount of a composition comprising a therapeutically effective amount of a compound of Formula I. A preferred embodiment of this aspect of the invention provides that the disorder being treated is a cellular proliferative disease, in particular wherein the cellular proliferative disease is cancer. A further preferred embodiment of this aspect of the invention provides a method wherein the cancer is selected from the group consisting of lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-Hodgkin lymphoma; melanoma; and villous colon adenoma.

Yet another aspect of the present invention provides a method of treating a disorder mediated, at least in part, by KSP in a mammalian patient comprising administering to a mammalian patient in need of such treatment a therapeutically effective amount of a composition comprising a therapeutically effective amount of a compound of Formula I, and an additional agent. A preferred embodiment of this aspect provides a method wherein, the additional agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

Yet another aspect of the present invention provides a method for inhibiting KSP kinesin in a mammalian patient, wherein said method comprises administering to the patient an effective KSP-inhibiting amount of a compound of Formula I. A preferred embodiment of this aspect provides that the compound of Formula I be selected from:

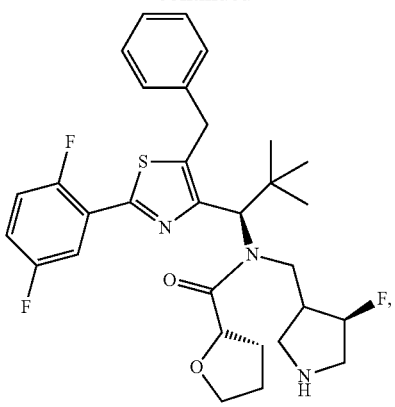

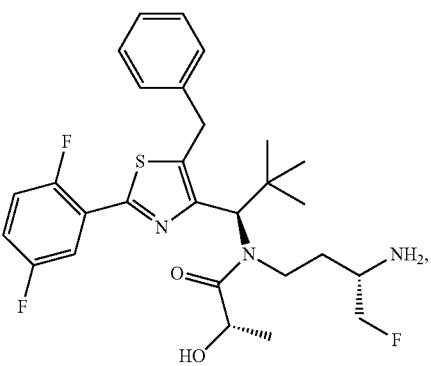

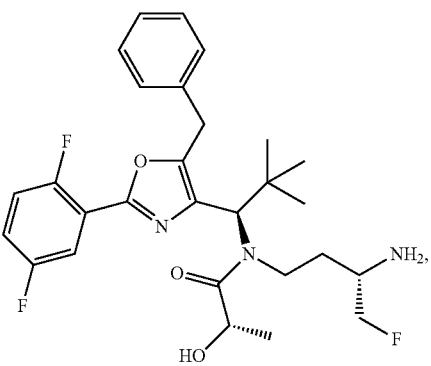

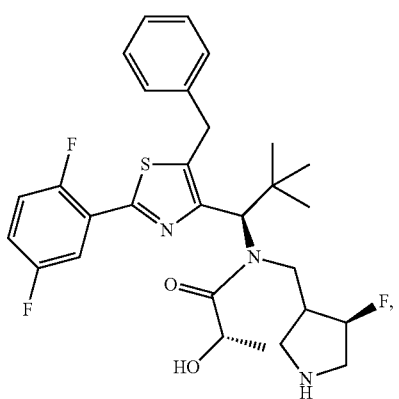

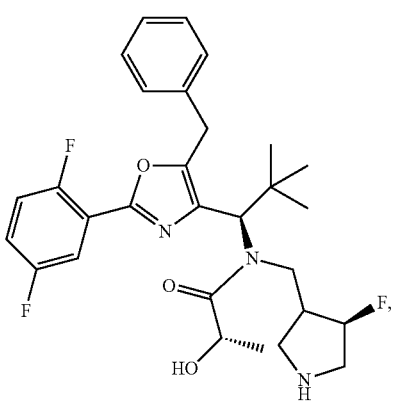

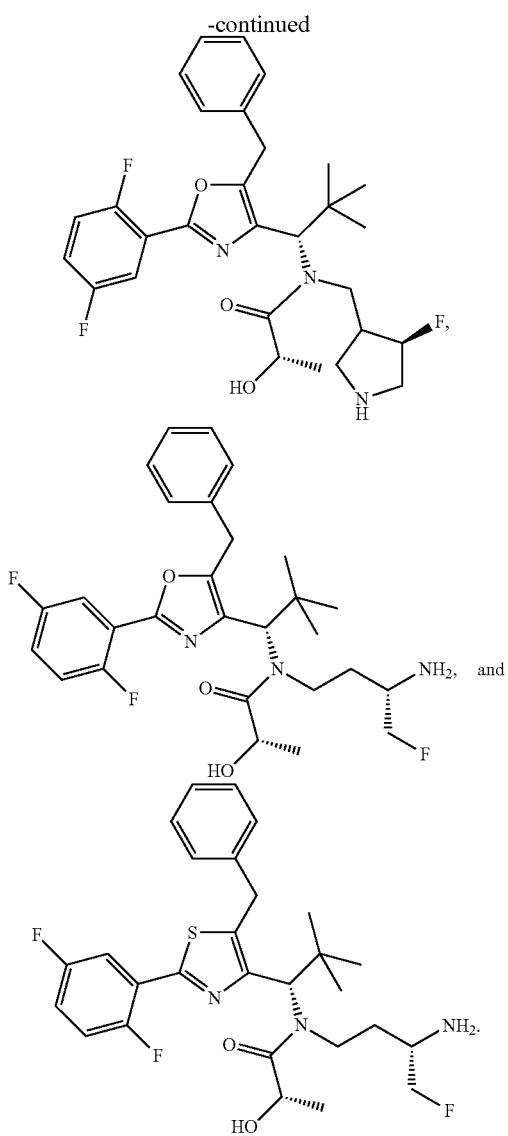

Representative Compounds of the Invention

Specific compounds within the scope of this invention are exemplified in Table 1 and 2 in the Experimental section.

B. Definitions and Overview

As discussed above, the present invention is directed in part to new substituted oxazole and thiazole compounds.

It is to be understood that the terminology used herein is for the purpose of describing particular embodiments only and is not intended to limit the scope of the present invention. It must be noted that as used herein and in the claims, the singular forms "a," and "the" include plural referents unless the context clearly dictates otherwise. In this specification and in the claims which follow, reference will be made to a number of terms which shall be defined to have the following meanings:

As used herein, "alkyl" refers to monovalent saturated aliphatic hydrocarbyl groups having from 1 to 6 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, spirocycloalkyl, heteroaryl, substituted heteroaryl, heterocyclic, substituted heterocyclic, —SO$_2$-alkyl, and —SO$_2$ substituted alkyl.

"Alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) or (—CH(CH$_3$)CH$_2$—) and the like.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, and substituted heterocyclic with the proviso that any hydroxy substitution is not attached to a vinyl (unsaturated) carbon atom.

"Amino" refers to the group —NH$_2$.

"Cyano" refers to the group —CN.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO$_2$-alkyl, —SO$_2$-substituted alkyl, and where R' and R" are joined, together with the nitrogen bound thereto to form a heterocyclic or substituted heterocyclic group provided that R' and R" are both not hydrogen. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' or R" is hydrogen.

"Nitro" refers to the group —NO$_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) in which the condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl ester, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl ($NH_2$—$SO_2$—), and substituted amino sulfonyl.

"Carboxyl" refers to —COOH or salts thereof.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

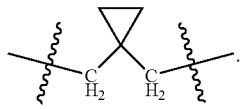

"Substituted cycloalkyl" refers to a cycloalkyl group, having from 1 to 5 substituents selected from the group consisting of alkyl, substituted alkyl, oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl ester, cycloalkyl, substituted cycloalkyl, heteroaryl, substituted heteroaryl, heterocyclic, substituted heterocyclic, —$SO_2$-alkyl and —$SO_2$-cycloalkyl "Halo" or "halogen" refers to fluoro, chloro, bromo and iodo and preferably is fluoro or chloro.

"Hydroxy" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 3 substituents selected from the same group of substituents defined for substituted aryl.

"Nitrogen-containing heteroaryl" and "nitrogen-containing substituted heteroaryl" refers to heteroaryl groups and substituted heteroaryl groups comprising at least one nitrogen ring atom and optionally comprising other non-nitrogen hetero ring atoms such as sulfur, oxygen and the like.

"Heterocycle" or "heterocyclic" or "heterocycloalkyl" or "heterocyclyl" refers to a saturated or unsaturated (but not aromatic) group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring. In one embodiment, the nitrogen and/or sulfur atom(s) of the heterocyclic group are optionally oxidized to provide for the N-oxide, sulfinyl, and sulfonyl moieties.

"Substituted heterocyclic" or "substituted heterocycloalkyl" or "substituted heterocyclyl" refers to heterocyclyl groups that are substituted with from 1 to 3 of the same substituents as defined for substituted cycloalkyl.

Examples of heterocyclyls and heteroaryls include, but are not limited to, azetidine, pyrrole, imidazole, pyrazole, oxazole, isoxazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitrogen-containing heterocyclic" and "nitrogen-containing substituted heterocyclic" refers to heterocyclic groups and substituted heterocyclic groups comprising at least one nitrogen ring atom and optionally comprising other non-nitrogen hetero ring atoms such as sulfur, oxygen and the like.

"Biological activity" as used herein refers to an inhibition concentration when tested in at least one of the assays outlined in any of Examples 9-11 and as defined in at least one example thereof.

As used herein, the term "pharmaceutically acceptable salts" refers to the nontoxic acid or alkaline earth metal salts of the compounds of Formula (I). These salts can be prepared in situ during the final isolation and purification of the compounds of Formula (I), or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napth-alenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of Formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which hydrolyze in vivo and include those that break down in the human body to leave the parent compound, a salt thereof, or a pharmaceutically active metabolite. Suitable ester groups include, for example, those derived from pharmaceutically acceptable aliphatic carboxylic acids, particularly alkenoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound or a pharmaceutically active metabolite of the above formula, for example by hydrolysis in blood. A discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein "anticancer agents" or "agent for the treatment of cancer" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art.

It is understood that in all substituted groups defined above, polymers arrived at by defining substituents with further substituents to themselves are not intended for inclusion herein. In such cases, the maximum number of such substituents is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxy group alpha to ethenylic or acetylenic unsaturation). Such impermissible substitution patterns are well known to the skilled artisan.

Compounds of this invention may exhibit stereoisomerism by virtue of the presence of one or more asymmetric or chiral centers in the compounds. The present invention contemplates the various stereoisomers and mixtures thereof. Depiction of the compounds of Formula (I), (Ia)-(Ie), (II), and (IIa)-(IIb) includes the stereoisomers thereof unless the stereochemistry of a particular stereocenter is indicated otherwise. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," *Pure Appl. Chem.* 45:13-30, 1976. Desired enantiomers can be obtained by chiral synthesis from commercially available chiral starting materials by methods well known in the art, or may be obtained from mixtures of the enantiomers by separating the desired enantiomer by using known techniques.

Compounds of this invention may also exhibit geometrical isomerism. Geometrical isomers include the cis and trans forms of compounds of the invention having alkenyl or alkenylenyl moieties. The present invention comprises the individual geometrical isomers and stereoisomers and mixtures thereof.

C. Compound Preparation

The compounds of this invention can be prepared from readily available starting materials using the following general methods and procedures. Unless otherwise indicated, the starting materials are commercially available and well known in the art. It will be appreciated that where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Second Edition, Wiley, New York, 1991, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

In one embodiment, provided is a method for preparing a compound of Formula (I) where X is O:

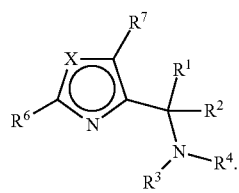

This method comprises:

a) heating a compound of Formula (IIIa) with a compound of Formula (IVa) to form a compound of Formula (Va), where $R^6$ and $R^7$ are previously defined and X is halogen.

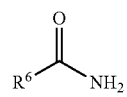
(IIIa)

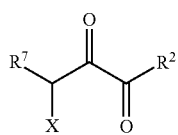
(IVa)

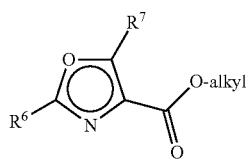
(Va)

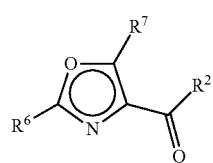
(Va')

b) reacting a compound of Formula (Va) under reduction conditions followed by oxidation reaction to give a compound of Formula (Va'), where $R^2$ is previously defined.

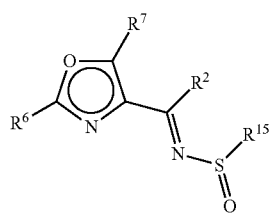
(VIa)

c) reacting a compound of Formula (Va') with sulfinamide (chiral or racemic) to form a compound of Formula (VIa) where $R^{15}$ is alkyl (substituted) or aryl (substituted).

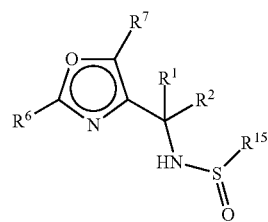
(VIIa)

d) reacting a compound of Formula (VIa) with metallated $R^1$ to form a compound of Formula (VIIa), where $R^1$ is previously defined.

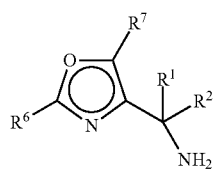
(VIIIa)

e) treating a compound of Formular (VIIa) under acidic condition to form a compound of Formula (VIIIa).

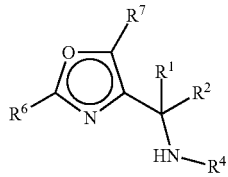
(IXa)

f) reacting a compound of Formula (VIIIa) with $R^4$—$X^4$ under coupling conditions or $R^{4a}$CHO under reductive animation conditions wherein $R^4$ is previously defined and $R^{4a}$CH$_2$— is $R^4$ and $X^4$ is a leaving group to form a compound of Formula (IXa).

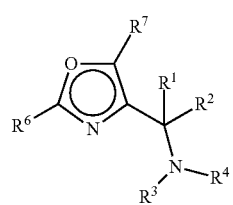

g) reacting a compound of Formula (IXa) with $R^3$—$X^3$ under coupling conditions wherein $R^3$ is previously defined and $X^3$ is a leaving group to form a compound of Formula (I) where X is O.

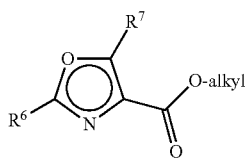
(Va)

In one embodiment provided is a method for preparing a compound of Formula (Va) by reacting (IIIa) with (IVa) in high temperature (100° C.). An example of this process for forming (IVa) where $R^6$ is 2,5-difluorobenzyl and $R^7$ is benzyl is shown in Step A of Example 4.

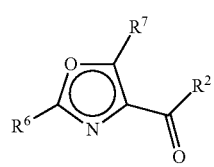
(Va')

In another embodiment provided is a method for preparing a compound of Formula (Va') from a compound of Formula (Va). An example of this process for forming (Va') where $R^6$ is 2,5-difluorobenzyl, $R^7$ is benzyl, and $R^2$ is hydrogen is shown in Step B and Step C of Example 4.

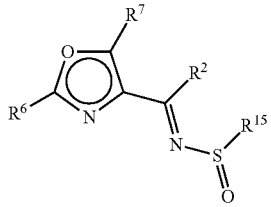
(VIa)

In one embodiment provided is a method for preparing a compound of Formula (VIa) by reacting (Va') with alkyl or aryl sulfinamide. Racemic t-Butylsulfinamide is used to get racemic mixture of (VIa). Ellman's chiral t-butylsulfinamide can be used for chiral induction to chiral (VIa). An example of this process for forming (VIa) where $R^6$ is 2,5-difluorobenzyl, $R^7$ is benzyl, $R^{15}$ is t-butyl, and $R^2$ is hydrogen is shown in Step D of Example 4.

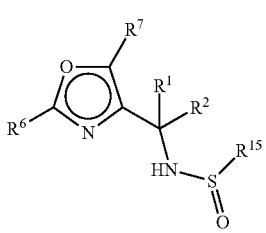
(VIIa)

In one embodiment provided is a method for preparing a compound of Formula (VIIa) by reacting (VIa) with metallated alkyl group. Alkyllithium is used to obtain racemic mixture of (VIIa) from racemic (VIa). Chiral (VIa) can react with alkyllithium leading to chiral (VIIa). Such conditions include use of a polar solvent such as tetrahydrofuran. The reaction is carried out at low temperature (−78° C.) under anhydrous conditions. An example of this process for forming (VIIa) where $R^6$ is 2,5-difluorobenzyl, $R^7$ is benzyl, $R^4$ and $R^{15}$ are t-butyl, and $R^2$ is hydrogen is shown in Step E of Example 4.

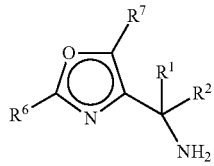
(VIIIa)

In another embodiment, provided is a method of preparing an intermediate compound of Formula (VIIIa) by exposing a compound of Formula (VIIa) to deprotection conditions. In one aspect when $R^{15}$ is t-butylsulfinyl, the protecting group is removed by exposure to acidic conditions such treatment with hydrochloric acid. An example of this deprotection is shown in Step F of Example 4.

In one embodiment, provided is a method of preparing an aldehyde intermediate $R^{4a}$CHO wherein $R^4$ and $R^{4a}$ are previously defined.

Scheme 1

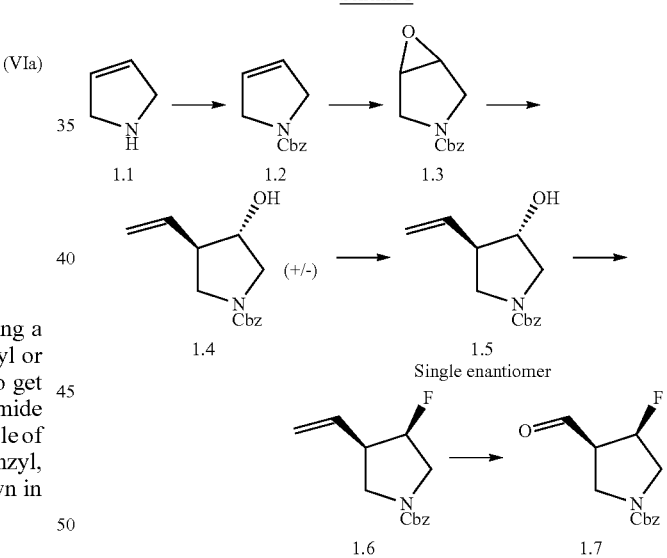

Scheme 1 illustrates the preparation of aldehyde 1.7 that can be used in the reductive amination step to prepare compounds of formula I, particularly compounds of formula I [wherein X=O, S]. Cyclic amine 1.1 is protected with Cbz group to give compound 1.2. Epoxide 1.3 is obtained from MCPBA epoxidation of compound 1.2. Epoxide gives racemic mixture of alcohol 1.4 by reacting vinylmagnesium bromide in the presence of copper bromide. Alcohol 1.5 as a single enantiomer is obtained by chiral column chromatography. Alcohol 1.5 is subjected to a fluorination condition to give vinyl fluoropyrrolidine 1.6. Vinyl fluoropyrrolidine 1.6 undergoes subsequent dihydroxylation/oxidative cleavage to give aldehyde 1.7. An example of this process is shown in Step H to L of Example 1.

In another embodiment, provided is a method for preparing an intermediate compound of Formula (IXa):

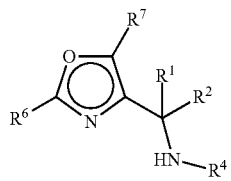

(IXa)

A compound of Formula (VIIIa) is reacted with $R^{4a}$CHO under reductive animation conditions wherein $R^4$ and $R^{4a}$ are previously defined to form a compound of Formula (IXa). Suitable reductive amination conditions include pre-mixing (VIIIa) with a reducing agent followed by addition of aldehyde $R^{4a}$CHO or reacting (VIIIa) with aldehyde $R^{4a}$CHO followed by addition of a reducing agent. In some aspects the solvent is a chlorinating compound such as dichloromethane and reducing agent is a borohydride such as triacetoxyborohydride. An example of such modifications is shown in Step G of Example 4.

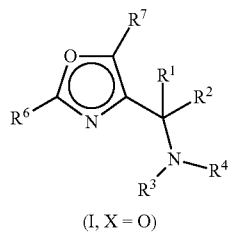

(I, X = O)

In another embodiment, provided is a method for preparing a compound of Formula (I) where X is O by reacting a compound of Formula (IXa) under suitable coupling conditions with $R^3$—$X^3$ wherein $R^3$ is previously defined and $X^3$ is a leaving group such as a halogen atom.

In some aspects $R^3$—$X^3$ is an acyl halide and the reaction is preformed in the presence of an organic base such as triethylamine. An example of such modifications is shown in Step H of Example 4.

Another embodiment, provides a method for preparing a compound of Formula (I) where X is S:

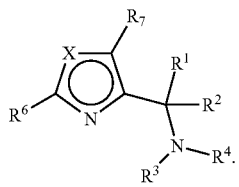

This method comprises:
a) converting a compound of Formula (IIIa) to a compound of Formula (IIIb) by reacting Lawesson's reagent where $R^6$ is previously defined.

(IIIb)

b) heating a compound of Formula (IIIb) with a compound of Formula (IVb) to form a compound of Formula (Vb), where $R^7$ is previously defined and X is halogen.

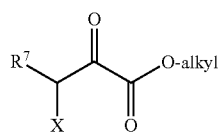

(IVb)

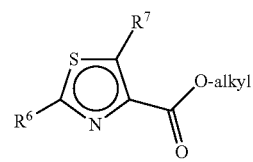

(Vb)

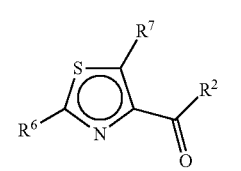

(Vb')

c) reacting a compound of Formula (Vb) under reduction conditions followed by oxidation reaction to give a compound of Formula (Vb'), where $R^2$ is previously defined.

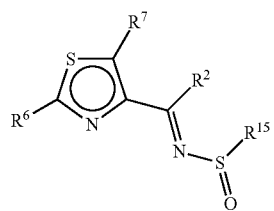

(VIb)

d) reacting a compound of Formula (Vb') with sulfinamide (chiral or racemic) to form a compound of Formula (VIb) where $R^{15}$ is alkyl (substituted) or aryl (substituted).

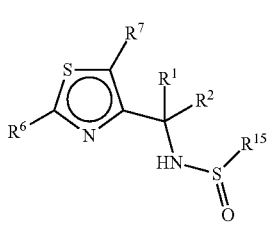

(VIIb)

e) reacting a compound of Formula (VIb) with metallated $R^1$ to form a compound of Formula (VIIb), where $R^1$ is previously defined.

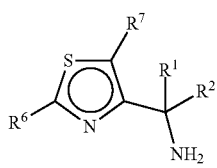
(VIIIb)

f) treating a compound of Formular (VIIb) under acidic condition to form a compound of Formula (VIIIb).

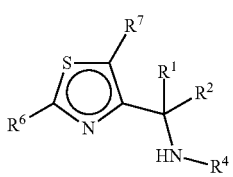
(IXb)

g) reacting a compound of Formula (VIIIb) with $R^4$—$X^4$ under coupling conditions or $R^{4a}$CHO under reductive animation conditions wherein $R^4$ is previously defined and $R^{4a}CH_2$— is $R^4$ and $X^4$ is a leaving group to form a compound of Formula (IXb).

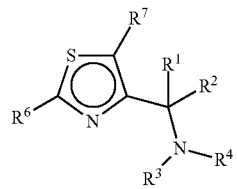

h) reacting a compound of Formula (IXb) with $R^3$—$X^3$ under coupling conditions wherein $R^3$ is previously defined and $X^3$ is a leaving group to form a compound of Formula (I) where X is S.

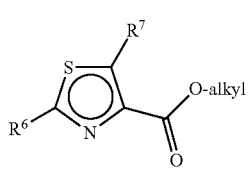
(Vb)

In one embodiment provided is a method for preparing a compound of Formula (Vb) by reacting (IIIb) with (IVb). An example of this process for forming (IVb) where $R^6$ is 2,5-difluorobenzyl and $R^7$ is benzyl is shown in Step B of Example 1.

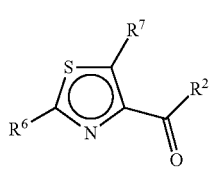
(Vb')

In another embodiment provided is a method for preparing a compound of Formula (Vb') from a compound of (Vb). An example of this process for forming (Vb') where $R^6$ is 2,5-difluorobenzyl, $R^7$ is benzyl, and $R^2$ is hydrogen is shown in Step C and Step D of Example 1.

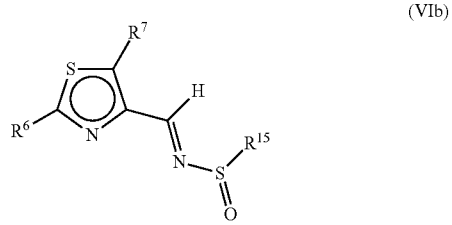
(VIb)

In one embodiment provided is a method for preparing a compound of Formula (VIb) by reacting (Vb') with alkyl or aryl sulfinamide. Racemic t-Butylsulfinamide can be used to get racemic mixture of (VIb). Ellman's chiral t-butylsulfinamide is used for chiral induction to chiral (VIb). An example of this process for forming (VIb) where $R^6$ is 2,5-difluorobenzyl, $R^7$ is benzyl, $R^{15}$ is t-butyl, and $R^2$ is hydrogen is shown in Step E of Example 1.

(VIIb)

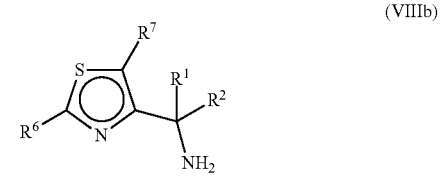

In one embodiment provided is a method for preparing a compound of Formula (VIIb) by reacting (VIb) with metallated alkyl group. Alkyllithium is used to obtain racemic mixture of (VIIb) from racemic (VIb). Chiral (VIb) can react with alkyllithium leading to chiral (VIIb). Such conditions include use of a polar solvent such as tetrahydrofuran. The reaction is carried out at low temperature (−78° C.) under anhydrous conditions. An example of this process for forming (VIIb) where $R^6$ is 2,5-difluorobenzyl, $R^7$ is benzyl, $R^4$ and $R^{15}$ are t-butyl, and $R^2$ is hydrogen is shown in Step F of Example 1.

(VIIIb)

[structure similar to VIIIb]

In another embodiment, provided is a method of preparing an intermediate compound of Formula (VIIIb) by exposing a compound of Formula (VIIb) to deprotection conditions. In one aspect when $R^{15}$ is t-butylsulfinyl, the protecting group is removed by exposure to acidic conditions such treatment with hydrochloric acid. An example of this deprotection is shown in Step G of Example 1.

In another embodiment, provided is a method for preparing an intermediate compound of Formula (IXb):

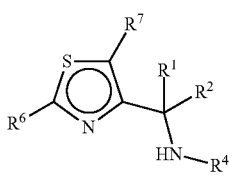
(IXb)

A compound of Formula (VIIIb) is reacted with $R^{4a}$CHO under reductive animation conditions wherein $R^4$ and $R^{4a}$ are previously defined to form a compound of Formula (IXb). Suitable reductive amination conditions include pre-mixing (VIIIb) with a reducing agent followed by addition of aldehyde $R^{4a}$CHO or reacting (VIIIb) with aldehyde $R^{4a}$CHO followed by addition of a reducing agent. In some aspects the solvent is a chlorinating compound such as dichloromethane and reducing agent is a borohydride such as triacetoxyborohydride. An example of such modifications is shown in Step N of Example 1.

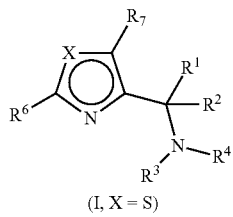
(I, X = S)

In another embodiment, provided is a method for preparing a compound of Formula (I) where X is S by reacting a compound of Formula (IXa) under suitable coupling conditions with $R^3$—$X^3$ wherein $R^3$ is previously defined and $X^3$ is a leaving group such as a halogen atom. In some aspects $R^3$—$X^3$ is an acyl halide and the reaction is preformed in the presence of an organic base such as triethylamine. An example of such modifications is shown in Step Q of Example 1.

D. Pharmaceutical Formulations

When employed as pharmaceuticals, the compounds of the subject invention are usually administered in the form of pharmaceutical compositions. These compositions can be administered by a variety of routes including oral, parenteral, transdermal, topical, rectal, and intranasal. These compounds are effective, for example, as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 1 to about 500 mg, usually about 5 to about 100 mg, occasionally about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the condition being treated, the chosen route of administration, the actual compound administered, the age, weight, and response of the individual patient, the severity of the patient's symptoms, and the like.

In therapeutic use for treating, or combating, cancer in mammals, the compounds or pharmaceutical compositions thereof will be administered by any appropriate route, such as orally, topically, transdermally, and/or parenterally at a dosage to obtain and maintain a concentration, that is, an amount, or blood-level of active component in the mammal undergoing treatment that will be therapeutically effective. Generally, such therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%)/ Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
|---|---|
| Active Ingredient | 5.0 mg |
| Corn Oil | 1.0 mL |

Formulation Example 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

An illustrative example of an intravenous formulation may be prepared as follows:

| Ingredient | Quantity |
|---|---|
| Active Ingredient | 250 mg |
| Isotonic saline | 1000 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat.

No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mack Publishing Company, Philadelphia, Pa., 17th ed. (1985).

E. Dosage and Administration

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Compounds of the instant invention are useful for inhibiting or treating a disorder mediated, at least in part, by the activity of KSP. In one aspect, the disorder that is mediated, at least in part by KSP, is a cellular proliferative disorder. The term "cellular proliferative disorder" or "cell proliferative disorder" refers to diseases including, for example, cancer, tumor, hyperplasia, restenosis, cardiac hypertrophy, immune disorder and inflammation. The present invention provides methods of treating a human or mammalian subject in need of such treatment, comprising administering to the subject a therapeutically effective amount of a compound of formula I or II, either alone or in combination with other anticancer agents.

The compounds of the invention are useful in vitro or in vivo in inhibiting the growth of cancer cells. The term "cancer" refers to cancer diseases including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

Cancer also includes tumors or neoplasms selected from the group consisting of carcinomas, adenocarcinomas, sarcomas, and hematological malignancies.

Additionally, the type of cancer can be selected from the group consisting of growth of solid tumors/malignancies, myxoid and round cell carcinoma, locally advanced tumors, human soft tissue carcinoma, cancer metastases, squamous cell carcinoma, esophageal squamous cell carcinoma, oral carcinoma, cutaneous T cell lymphoma, Hodgkin's lymphoma, non-Hodgkin's lymphoma, cancer of the adrenal cortex, ACTH-producing tumors, nonsmall cell cancers, breast cancer, gastrointestinal cancers, urological cancers, malignancies of the female genital tract, malignancies of the male genital tract, kidney cancer, brain cancer, bone cancers, skin cancers, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

A compound or composition of this invention may be administered to a mammal by a suitable route, such as orally, intravenously, parenterally, transdermally, topically, rectally, or intranasally.

Mammals include, for example, humans and other primates, pet or companion animals, such as dogs and cats, laboratory animals, such as rats, mice and rabbits, and farm animals, such as horses, pigs, sheep, and cattle.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and organization relative to one another and to surrounding tissues. This property is called "anaplasia."

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the compounds during incubation with peptidases or human plasma or serum.

For diagnostic purposes, a wide variety of labels may be linked to the compounds, which may provide, directly or indirectly, a detectable signal. Thus, the compounds and/or compositions of the subject invention may be modified in a variety of ways for a variety of end purposes while still retaining biological activity. In addition, various reactive sites may be introduced for linking to particles, solid substrates, macromolecules, and the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the progression or symptoms of the disease and its complications. An amount adequate to accomplish this is defined as "therapeutically effective dose." Amounts effective for this use will depend on the disease condition being treated as well as by the judgment of the attending clinician depending upon factors such as the severity of the disease, disorder or condition, the age, weight and general condition of the patient, and the like.

The compounds administered to a patient are typically in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between about 3 and 11, more preferably from about 5 to 9 and most preferably from about 7 to 8. It will be understood that use of certain of the foregoing excipients, carriers, or stabilizers will result in the formation of pharmaceutical salts.

The therapeutic dosage of the compounds and/or compositions of the present invention will vary according to, for example, the particular use for which the treatment is made, the manner of administration of the compound, the health and condition of the patient, and the judgment of the prescribing physician. For example, for oral administration, the dose will typically be in the range of about 5 µg to about 50 mg per kilogram body weight per day, preferably about 1 mg to about 10 mg per kilogram body weight per day. In the alternative, for intravenous administration, the dose will typically be in the range of about 5 µg to about 50 mg per kilogram body weight, preferably about 500 µg to about 5000 µg per kilogram body weight. Alternative routes of administration contemplated include, but are not limited to, intranasal, transdermal, inhaled, subcutaneous and intramuscular. Effective doses can be extrapolated from dose-response curves derived from in vitro or animal model test systems.

In general, the compounds and/or compositions of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound and/or composition used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of activity) as determined in cell culture. Such information can be used to more accurately determine useful doses in humans. Levels in plasma may be measured, for example, by high performance liquid chromatography.

The following synthetic and biological examples are offered to illustrate this invention and are not to be construed in any way as limiting the scope of this invention.

EXAMPLES

Referring to the examples that follow, compounds of the present invention were synthesized using the methods described herein, or other methods, which are well known in the art. It is understood that compounds not prepared or analyzed may be prepared or analyzed using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LC/MS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses were reported as those of the protonated parent ions.

GC/MS analysis is performed on a Hewlett Packard instrument (HP6890 Series gas chromatograph with a Mass Selective Detector 5973; injector volume: 1 mL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.).

Melting points are determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, EtOAc, hexane, acetone, aqueous hydroxyamine and triethyl amine. Typical solvents employed for the reverse phase HPLC were varying concentrations of acetonitrile and water with 0.1% trifluoroacetic acid. Unless otherwise stated all temperatures are in degrees Celsius. Also, in these examples and elsewhere, abbreviations have the following meanings:

AcOH=acetic acid
aq.=aqueous
ATP=adenosine triphosphate
Bac=tert-butyloxycarbonyl
BSA=bovine serum albumin
CAM=ceric ammonium molybdate
DCM=dichloromethane
DIAD=diisopropyl azodicarboxylate
DIBAL=diisobutylaluminum hydride
DIEA=diisopropylethylamine
DIPEA=diisopropylethylamine
DMAP=dimethylaminopyridine
DMF=dimethylformamide
DMSO=dimethylsulfoxide
DTT=dithiothreitol
eq.=equivalents
Et$_2$O=diethyl ether
Et$_3$N=triethyl amine
EtOAc=ethyl acetate
EtOH=ethanol
g=gram
h=hour
HPLC=high performance liquid chromatography
L=liter
LC/MS=liquid chromatography/mass spectroscopy
M=molar
m=meter
m/z=mass/charge ratio
MeNH$_2$=methyl amine
mg=milligram
min=minute
mL=milliliter
mm=millimeter
mM=millimolar
mmol=millimole
mol=mole
N=normal
nm=nanometer
nM=nanomolar
NMR=nuclear magnetic resonance
PPh$_3$=triphenyl phosphine
PhCF$_3$=trifluoromethylbenzene
psi=pounds per square inch
RT=room temperature
sat.=saturated
TEA=triethylamine
THF=tetrahydrofuran
TFA=trifluoroacetic acid
TLC=thin layer chromatography
TMS=trimethylsilyl
TMSCl=trimethylsilyl chloride=
μg=microgram
μL=microliter
μM=micromolar
uplc=Ultra performance liquid chromatography Example 1

(S)-N-((R)-1-(5-benzyl-2-(2,5-difluorophenyl)thiazol-4-yl)-2,2-dimethylpropyl)-N-(((3S,4R)-4-fluoropyrrolidin-3-yl)methyl)-2-hydroxypropanamide

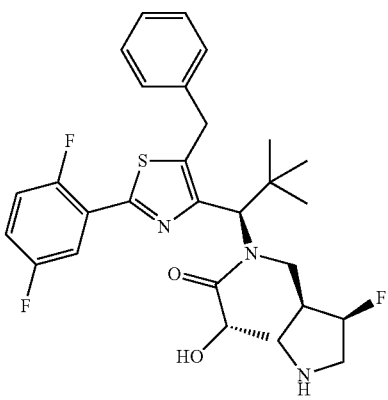 [SMILES: C[C@H](O)C(=O)N(C[C@@H]1CNC[C@@H]1F)[C@@H](c1nc(-c2cc(F)ccc2F)sc1Cc1ccccc1)C(C)(C)C]

Step A: α-Bromination of Ethyl 2-oxo-4-phenylbutanoate

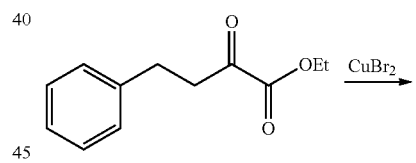

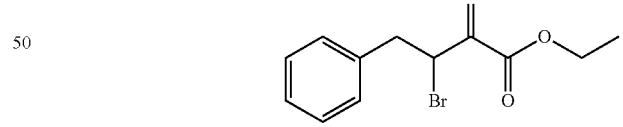

To a solution of ethyl 2-oxo-4-phenylbutanoate (10 g, 48.5 mmol) in EtOAc (323 mL) and CHCl$_3$ (162 mL) was added copper(II) bromide (32.5 g, 145 mmol). The reaction mixture was refluxed for 6 h. After cooled down, the reaction mixture was filtered through silica gel, washed with EtOAc, and concentrated. The crude product was purified by column chromatography to yield ethyl 3-bromo-2-oxo-4-phenylbutanoate (15.0 g, >99%) as light yellow oil. $^1$H NMR (CDCl$_3$, 400 MHz): δ 7.42-7.28 (2H, m), 7.28-7.19 (3H, m), 5.27 (1H, m), 4.35 (2H, m), 3.54 (1H, m), 3.25 (1H, m), 1.37 (3H, m). LC/MS (uplc): MH$^+$ 269.1 (−18), 0.79 min.

Step B: Synthesis of Thiazole Core

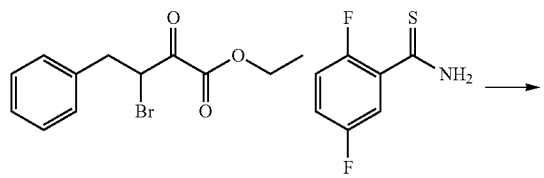

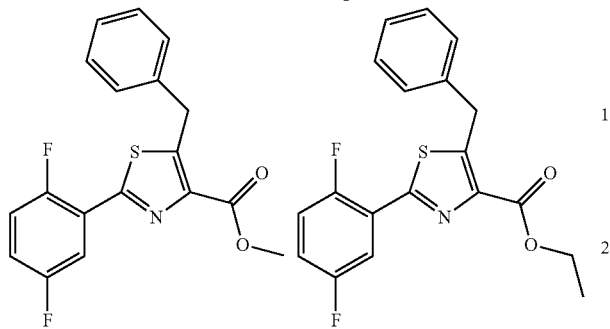

To a solution of ethyl 3-bromo-2-oxo-4-phenylbutanoate (13.8 g, 48.4 mmol) in MeOH (161 mL) was slowly added 2,5-difluorobenzothioamide (8.38 g, 48.4 mmol) at room temperature. The reaction mixture was then refluxed for overnight. After cooled down, white precipitate was filtered, washed by cold ethanol and dried. A mixture of methyl 5-benzyl-2-(2,5-difluorophenyl)thiazole-4-carboxylate and ethyl 5-benzyl-2-(2,5-difluorophenyl)thiazole-4-carboxylate (10.5 g, 61%) was obtained as white solid. LC/MS (uplc): MW 346.1, 1.21 min for methyl ester; 360.1, 1.27 min for ethyl ester.

Step C: Reduction of Thiazole Esters

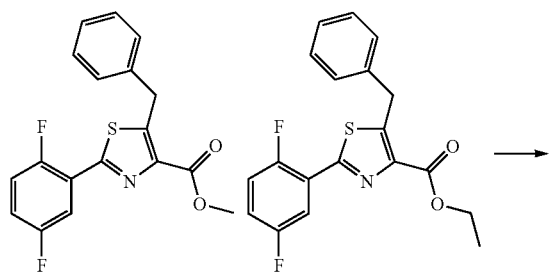

To a solution of a mixture of methyl 5-benzyl-2-(2,5-difluorophenyl)thiazole-4-carboxylate and ethyl 5-benzyl-2-(2,5-difluorophenyl)thiazole-4-carboxylate (7.8 g, 21.70 mmol) in THF (72.3 mL) was slowly added LiBH$_4$ (0.946 g, 43.4 mmol) at room temperature. The reaction mixture was stirred for overnight. After quenched with water, the reaction mixture was extracted with EtOAc. The organic layers was washed with saturated NaHCO$_3$ solution and brine, dried over anhydrous Na$_2$SO$_4$, filtered, and concentrated. The crude product was purified by column chromatography to yield (5-benzyl-2-(2,5-difluorophenyl)thiazol-4-yl)methanol (6.66 g, 97%) as white solid. LC/MS (uplc): MH$^+$ 318.2, 1.03 min.

Step D: Oxidation of Thiazole Alcohol

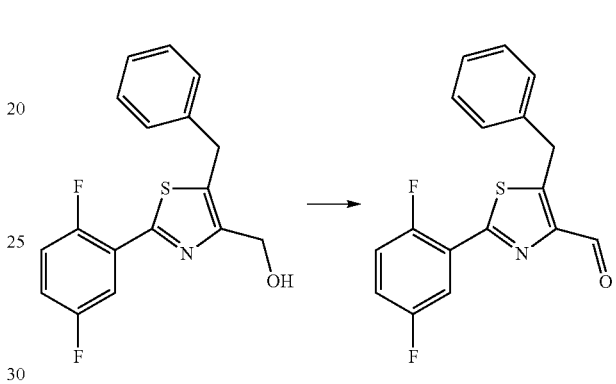

To a solution of (5-benzyl-2-(2,5-difluorophenyl)thiazol-4-yl)methanol (6.66 g, 20.99 mmol) in dichloromethane (70.0 mL) was added Dess-Martin periodinane (13.35 g, 31.5 mmol). The reaction mixture was stirred at room temperature for overnight. 200 mL of saturated NaHCO$_3$ solution and saturated Na$_2$S$_2$O$_3$ solution (8:1) was added for quenching the reaction. After stirred for 1 h, the reaction mixture was extracted by EtOAc. The organic layers was washed with water and brine, dried over anhydrous Na$_2$SO$_4$, filtered, and concentrated. The crude product was purified by column chromatography to yield 5-benzyl-2-(2,5-difluorophenyl)thiazole-4-carbaldehyde (5.3 g, 80%) as white solid. $^1$H NMR (CDCl$_3$, 400 MHz): δ 10.3 (1H, s), 8.01 (1H, m), 7.36-7.17 (5H, m), 7.16-7.07 (2H, m), 4.64 (2H, s). LC/MS (uplc): MH$^+$ 316.2, 1.21 min.

Step E: Synthesis of t-Butyl Sulfinimine

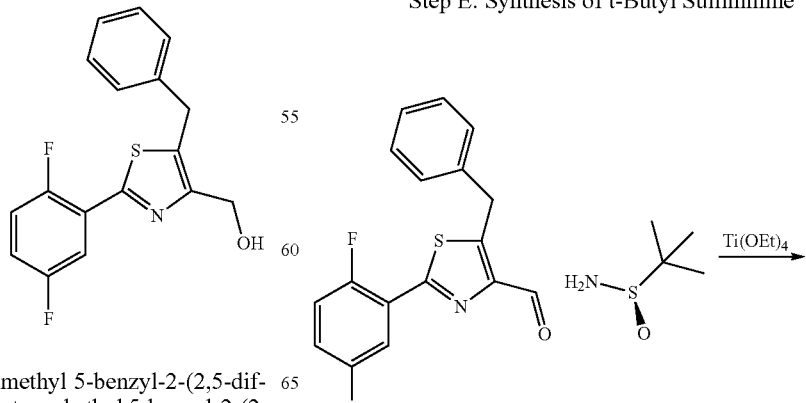

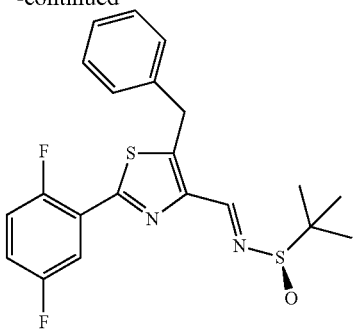

To a solution of 5-benzyl-2-(2,5-difluorophenyl)thiazole-4-carbaldehyde (5.2 g, 16.49 mmol) in THF (55.0 mL) was added (R)-(+)-t-butylsulfinamide (2.2 g, 18.14 mmol), and Ti(OEt)$_4$ (7.52 mL, 36.3 mmol). The reaction mixture was stirred for 4 h at room temperature. The reaction mixture was diluted with brine (50 mL) and EtOAc (70 mL) followed by addition of Celite®. Then, the mixture was vigorously stirred for 1 h, and filtered. The filtrate was extracted by EtOAc. The organic layers was washed with water and brine, dried over anhydrous Na$_2$SO$_4$, filtered, and concentrated. The crude product was purified by automatic column chromatography to yield (R)—N-((5-benzyl-2-(2,5-difluorophenyl)thiazol-4-yl)methylene)-2-methylpropane-2-sulfinamide (6.5 g, 94%) as pale yellow solid. $^1$H NMR (CDCl$_3$, 400 MHz): δ 8.91 (1H, s), 8.04 (1H, m), 7.38-7.22 (5H, m), 7.16-7.05 (2H, m), 4.62 (2H, s), 1.25 (9H, s). LC/MS (uplc): MH$^+$ 419.1, 1.31 min.

Step F: Diastereoselective Addition Reaction of t-Butyl Lithium to t-Butyl Sulfinimine

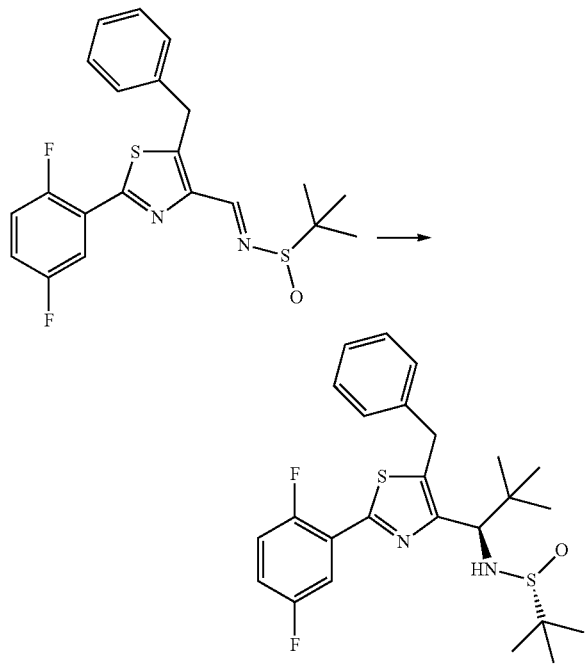

To a solution of (R)—N-((5-benzyl-2-(2,5-difluorophenyl)thiazol-4-yl)methylene)-2-methylpropane-2-sulfinamide (6.5 g, 15.53 mmol) in anhydrous THF (78 mL) was slowly added $^t$BuLi (1.7 M solution in pentane, 27.4 mL, 46.6 mmol) at −78° C. After the reaction mixture was stirred at −78° C. for 3 h, the reaction was quenched with MeOH (10 mL) followed by addition of saturated NH$_4$Cl solution (30 mL). Upon warming up to room temperature, the reaction mixture was stirred for 30 min and then extracted with EtOAc (250 mL). The organic layer was washed with water and brine, dried over anhydrous Na$_2$SO$_4$, filtered, and concentrated. The crude product was purified by automatic column chromatography to yield enantiomerically enriched (R)-N-((R)-1-(5-benzyl-2-(2,5-difluorophenyl)thiazol-4-yl)-2,2-dimethylpropyl)-2-methylpropane-2-sulfinamide (3.93 g, 53.1%) as a pale yellow solid. Only single diastereomer was formed and isolated. $^1$H NMR (CDCl$_3$, 400 MHz): δ 7.87 (1H, m), 7.37-7.29 (3H, m), 7.27-7.21 (2H, m), 7.11-6.96 (2H, m), 4.43-4.28 (2H, m), 4.24-4.09 (2H, m), 1.28 (9H, s), 1.00 (9H, s). LC/MS (uplc): MH$^+$ 477.2, 1.44 min.

Step G: Deprotection of 1-Butyl Sulfinyl Group

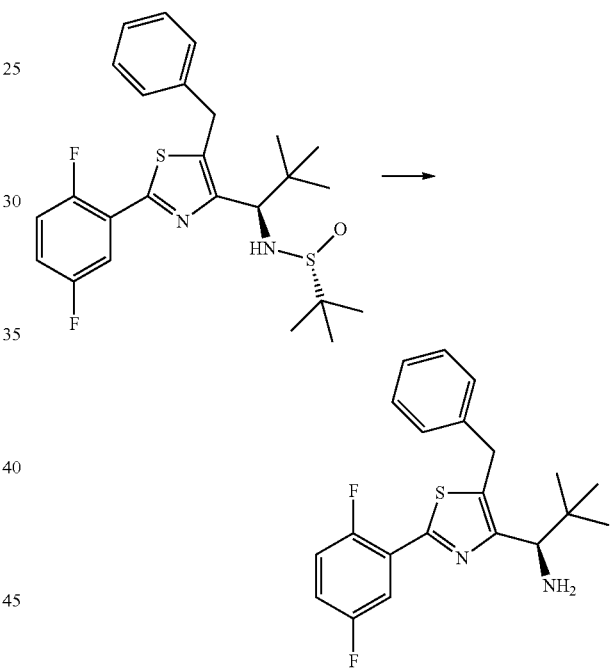

To a solution of (R)-N-((R)-1-(5-benzyl-2-(2,5-difluorophenyl)thiazol-4-yl)-2,2-dimethylpropyl)-2-methylpropane-2-sulfinamide (53 mg, 0.111 mmol) in THF (200 μL) was added MeOH (55.6 μL) and 4 M HCl in dioxane (55.6 μL, 0.222 mmol). The reaction mixture was stirred at room temperature for 1 h. After quenched with saturated Na$_2$CO$_3$ solution and diluted with EtOAc, the reaction mixture was stirred for 15 min and extracted with EtOAc. The organic layer was washed with water and brine, dried over anhydrous Na$_2$SO$_4$, filtered, and concentrated. The crude (R)-1-(5-benzyl-2-(2,5-difluorophenyl)thiazol-4-yl)-2,2-dimethylpropan-1-amine was obtained in 99% yield (41 mg), which was used for the next step without further purification (a major side product, methyl 2-methylpropane-2-sulfinate, was completely removed under high vacuum). $^1$H NMR (CDCl$_3$, 400 MHz): δ 7.96 (1H, m), 7.35-7.29 (2H, m), 7.28-7.22 (3H, m), 7.08 (1H, m), 7.0 (1H, m), 4.18 (2H, m), 3.8 (1H, s), 1.73 (2H, bs), 1.02 (9H, s). LC/MS (uplc): MH$^+$ 356.2, 1.08 min.

Step H: Cbz Protection of Dihydropyrrole

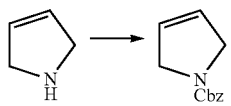

To a solution of 2,5-dihydro-1H-pyrrole (30 g, 434 mmol) in dioxane (0.43 M solution) was added CbzOSu (130 g, 521 mmol). After being stirred at room temperature for 18 h, the reaction mixture was concentrated to around 300 mL, diluted with 1000 mL of EtOAc. The organic layer was washed with water and brine, dried over anhydrous $Na_2SO_4$, filtered, and concentrated in vacuo. The desired benzyl 2,5-dihydro-1H-pyrrole-1-carboxylate was obtained in 91% yield (80.0 g) as a colorless oil by flash column chromatography. $^1$H NMR ($CDCl_3$, 400 MHz): δ 7.32 (5H, m), 5.80 (2H, m), 5.77 (2H, s), 4.22 (4H, m). LC/MS (uplc): $MH^+$ 204.2, 160.1 (−44), 0.86 min.

Step I: Epoxidation of Alkene

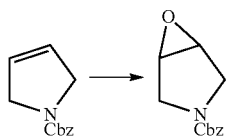 [SMILES: O=C(OCc1ccccc1)N1CC=CC1 ; O=C(OCc1ccccc1)N1CC2OC2C1]

To a solution of benzyl 2,5-dihydro-1H-pyrrole-1-carboxylate (33 g, 163 mmol) in dichloromethane (0.3 M solution) was added MCPBA (44 g, 340 mmol, 77% from Aldrich). After the reaction mixture was stirred at room temperature for 18 h, 500 mL of saturated $Na_2CO_3$ aqueous solution was added and the resulting mixture was stirred at room temperature for 1 h. The organic layer was separated, washed with water and brine, dried over anhydrous $Na_2SO_4$, filtered, and concentrated in vacuo. The desired product as a yellow oil was obtained in 83% yield (29.5 g) by flash column chromatography. $^1$H NMR ($CDCl_3$, 400 MHz): b 3.38 (2H, m), 3.68 (2H, m), 3.87 (2H, m), 5.11 (2H, s), 7.33 (5H, m). LC/MS (uplc): $MH^+$ 220.0, 0.69 min.

Step J: Ring Opening of Epoxide

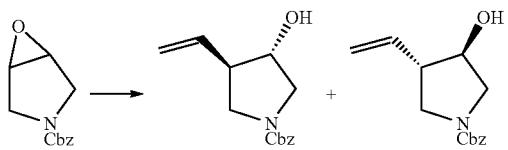 [SMILES: O=C(OCc1ccccc1)N1CC2OC2C1 ; C=C[C@@H]1CN(C(=O)OCc2ccccc2)C[C@H]1O ; C=C[C@H]1CN(C(=O)OCc2ccccc2)C[C@@H]1O]

To a solution of benzyl 6-oxa-3-azabicyclo[3.1.0]hexane-3-carboxylate (28.5 g, 130 mmol) and $CuBrSMe_2$ (26.7 g, 130 mmol) in anhydrous THF (260 mL, 0.5 M solution) at −40° C. was slowly added vinyl magnesium bromide (520 mL, 1.0 M solution in THF). The reaction mixture was then warmed up to −20° C. for 2 h. After quenched with saturated $NH_4Cl$ aqueous solution (200 mL), the reaction mixture was extracted with EtOAc (500 mL). The organic layer was washed with water and brine, dried over anhydrous $Na_2SO_4$, filtered and concentrated in vacuo. The desired racemic mixture of trans-(±)-benzyl 3-hydroxy-4-vinylpyrrolidine-1-carboxylate was obtained in 48% yield (15.5 g) as a yellow oil by flash column chromatography. $^1$H NMR ($CDCl_3$, 400 MHz): δ 2.71 (1H, m), 3.28 (2H, m), 3.72 (2H, m), 4.11 (1H, m), 5.14 (2H, s), 5.16-5.23 (2H, m), 5.69 (1H, m), 7.33 (5H, m). LC/MS (uplc): $MH^+$ 248.0, 0.78 min.

Step K: Resolution of Trans-(±)-Hydroxyl Vinylpyrrolidine

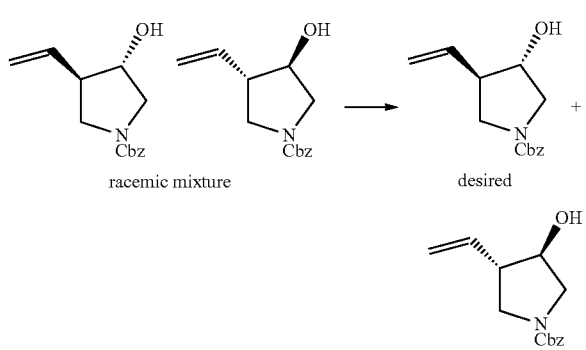

racemic mixture          desired

The racemic mixture of trans-(±)-benzyl 3-hydroxy-4-vinylpyrrolidine-1-carboxylate (14 g) was resolved by using chiral HPLC. The desired enantiomerically enriched (3S,4R)-benzyl 3-hydroxy-4-vinylpyrrolidine-1-carboxylate (6.7 min; 6.3 g, >99.5% ee) and undesired (3R,4S)-benzyl 3-hydroxy-4-vinylpyrrolidine-1-carboxylate (9.3 min; 6.7 g, 99.5% ee) were obtained.

Step L: Fluorination of Hydroxyl Vinylpyrrolidine

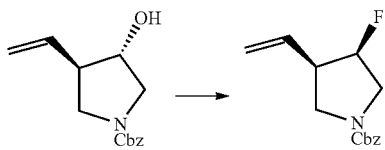 [SMILES: C=C[C@@H]1CN(C(=O)OCc2ccccc2)C[C@H]1O ; C=C[C@@H]1CN(C(=O)OCc2ccccc2)C[C@@H]1F]

To a solution of (3S,4R)-benzyl 3-hydroxy-4-vinylpyrrolidine-1-carboxylate (5.0 g, 20.2 mmol) in $PhCF_3$ (81 mL, 0.25 M solution) was added N,N-diisopropylethylamine (53 mL, 303 mmol), triethylamine trihydrofluoride (19.8 mL, 121 mmol) and perfluoro-1-butanesulfonyl fluoride (PBSF, 3.6 mL, 20.2 mmol). The resulting mixture was stirred at room temperature. After 60 and 120 minutes, additional perfluoro-1-butanesulfonyl fluoride (3.6 mL, 20.2 mmol) was added. After 18 hours, the reaction mixture was transferred to a separatory funnel and was washed twice with 50 mL of 1.0 N HCl (Caution! lots of heat produced), twice with saturated $NaHCO_3$ aqueous solution, and once with $H_2O$ and brine. The organic phase was dried over anhydrous $Na_2SO_4$, filtered and concentrated to provide a crude brown oil. The pure (3R,4R)-benzyl 3-fluoro-4-vinylpyrrolidine-1-carboxylate was obtained in 81% yield (4.1 g) as a yellow oil by flash column chromatography. $^1$H NMR ($CDCl_3$, 400 MHz): δ 7.37-7.25

(5H, m), 5.9 (1H, m), 5.24 (2H, m), 5.14 (2H, m), 5.03 (1H, m), 3.9-3.5 (3H, m), 3.53 (1H, m), 2.83 (1H, m). LC/MS (uplc): MH+ 250.0, 0.93 min.

Step M: Oxidative Cleavage of Vinyl Fluoropyrrolidine

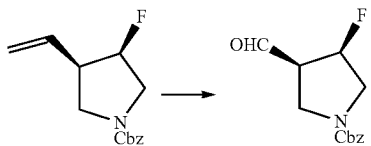 [SMILES: C=C[C@@H]1CN(C(=O)OCc2ccccc2)C[C@@H]1F ; O=C[C@@H]1CN(C(=O)OCc2ccccc2)C[C@@H]1F]

To a solution of (3R,4R)-benzyl 3-fluoro-4-vinylpyrrolidine-1-carboxylate (1.78 g, 7.15 mmol) in CH$_3$OH and H$_2$O (2:1, 178 mL, 0.04 M solution) was added a solution of OsO$_4$ in H$_2$O (3 mL of a 4% w/v solution, 0.5 mmol). NaIO$_4$ (4.6 g, 21.5 mmol) was then added in a single portion and the resulting mixture was stirred at room temperature. After 2 hours, the mixture was filtered to remove precipitated white solids and the filter cake was washed with EtOAc. The filtrate was concentrated in vacuo to remove the majority of the organic solvents. The residue was extracted with three portions of EtOAc and the combined organic layer was dried over anhydrous Na$_2$SO$_4$, filtered and concentrated. The crude (3R,4S)-benzyl 3-fluoro-4-formylpyrrolidine-1-carboxylate was used for the next step without further purification. LC/MS (uplc): MH+ 208.2 (−44), 252.0, 0.69 min.

Step N: Reductive Amination

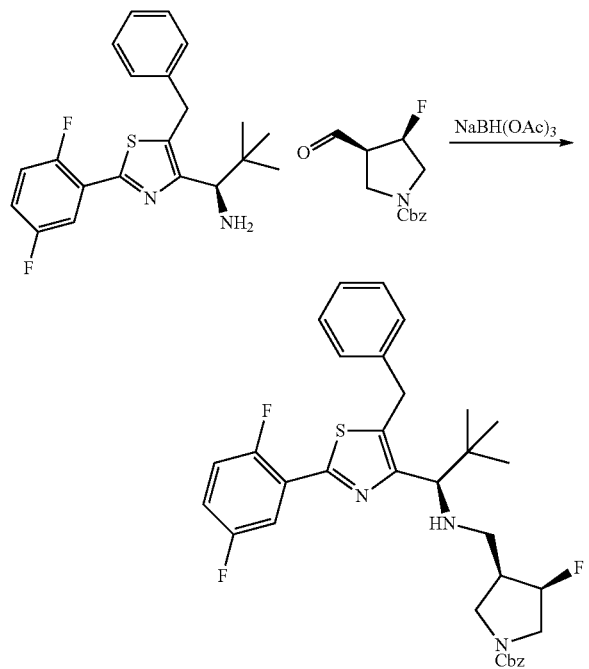

To a solution of (R)-1-(5-benzyl-2-(2,5-difluorophenyl)thiazol-4-yl)-2,2-dimethylpropan-1-amine (140 mg, 0.378 mmol) in CH$_2$Cl$_2$ (7.0 mL) was added NaBH(OAc)$_3$ (400 mg, 1.89 mmol). To this solution, the crude (3R,4S)-benzyl 3-fluoro-4-formylpyrrolidine-1-carboxylate (obtained from 2.0 equiv. of (3R,4R)-benzyl 3-fluoro-4-vinylpyrrolidine-1-carboxylate) in CH$_2$Cl$_2$ (1.0 mL) was added over 3 minute at room temperature. After stirred for 20 min, the reaction mixture was quenched with saturated NaHCO$_3$ solution and extracted with EtOAc. The organic layer was washed with water and brine, dried over anhydrous Na$_2$SO$_4$, filtered and concentrated. The crude product was purified on preparative reverse phase HPLC. The combined fractions of the product were neutralized with saturated NaHCO$_3$ solution, which was then extracted with EtOAc. The organic layer was dried over anhydrous sodium sulfate, filtered and concentrated in vacuo to yield (3R,4R)-benzyl 3-(((R)-1-(5-benzyl-2-(2,5-difluorophenyl)thiazol-4-yl)-2,2-dimethylpropylamino)methyl)-4-fluoropyrrolidine-1-carboxylate (138 mg, 60%). LC/MS (uplc) MH+ 608.3, 1.14 min.

Step O: Amide Bond Formation

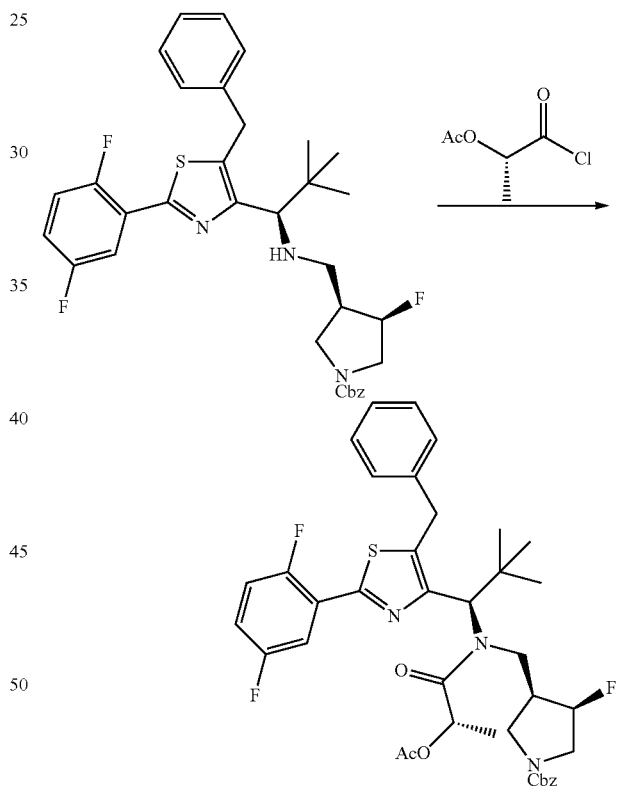

to a solution of (3R,4R)-benzyl 3-(((R)-1-(5-benzyl-2-(2,5-difluorophenyl)thiazol-4-yl)-2,2-dimethylpropylamino)methyl)-4-fluoropyrrolidine-1-carboxylate (130 mg, 0.214 mmol) in dichloromethane (2.1 mL, 0.1 M solution) at room temperature was added N,N-diisopropylethylamine (112 μL, 0.64 mmol). (S)-1-Chloro-1-oxopropan-2-yl acetate (54.2 μL, 0.428 mmol) was then added dropwise over 2 min. The resulting solution was stirred at room temperature for 2 h. The reaction mixture was quenched with saturated NaHCO$_3$ solution and extracted with EtOAc. The organic layer was washed with water and brine, dried over anhydrous sodium sulfate and filtered. After the volatile organic materials were removed in vacuo, the crude product was purified on flash column chromatography to yield (3R,4R)-benzyl 3-(((S)-2-acetoxy-N-((R)-1-(5-benzyl-2-(2,5-difluorophenyl)thiazol-4-yl)-2,2-dimethylpropyl)propanamido)methyl)-4-fluoropyrrolidine-1-carboxylate (115 mg, 75%). NMR (CDCl₃, 400 MHz): δ 7.85 (1H, m), 7.37-7.24 (7H, m), 7.21 (1H, m), 7.09 (2H, m), 7.05 (1H, m), 6.96 (1H, m), 6.1 (1H, m), 5.4 (2H, m), 5.28 (1H, m), 4.82 (2H, m), 4.19-3.97 (3H, m), 3.70-3.49 (2H, m), 3.13 (1H, m), 2.76 (1H, m), 2.52 (1H, m), 2.18 (3H, s), 1.61 (3H, m), 0.99 (9H, s). LC/MS (uplc): MH⁺ 722.3, 1.40 min.

Step P: Deacetylation

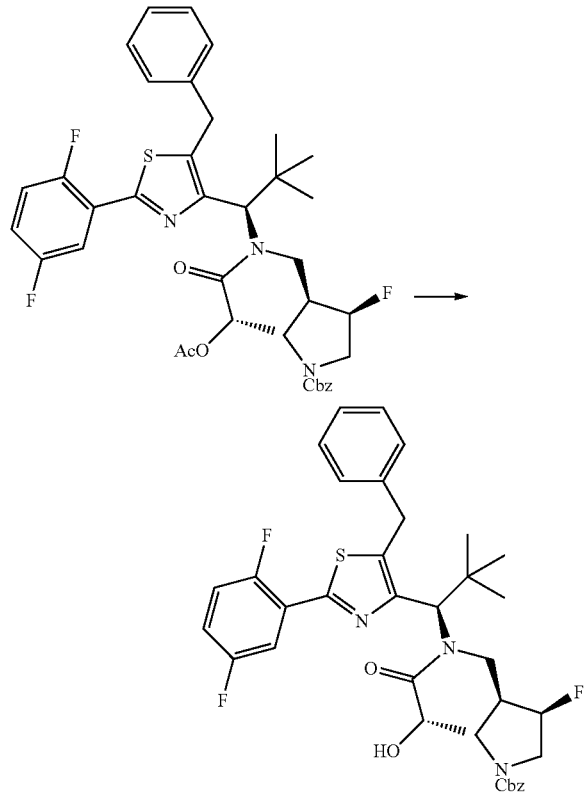

To a solution of (3R,4R)-benzyl 3-(((S)-2-acetoxy-N-((R)-1-(5-benzyl-2-(2,5-difluorophenyl)thiazol-4-yl)-2,2-dimethylpropyl)propanamido)methyl)-4-fluoropyrrolidine-1-carboxylate (40 mg, 0.055 mmol) in methanol (3.5 mL, 0.11 M solution) was added 1 M LiOH solution (0.083 mL, 0.083 mmol) at room temperature. After stirred for 30 min, the reaction mixture was neutralized with 1 N HCl solution (0.083 mL, 0.083 mmol) and then extracted with EtOAc. The organic layer was washed with water and brine, dried over anhydrous sodium sulfate, filtered, and concentrated in vacuo. The crude (3R,4R)-benzyl 3-(((S)-N-((R)-1-(5-benzyl-2-(2,5-difluorophenyl)thiazol-4-yl)-2,2-dimethylpropyl)-2-hydroxypropanamido)methyl)-4-fluoropyrrolidine-1-carboxylate (108 mg, >99%) was used for the next step with further purification. LC/MS (uplc): MH⁺ 680.4, 1.36 min.

Step Q: Cbz Deprotection

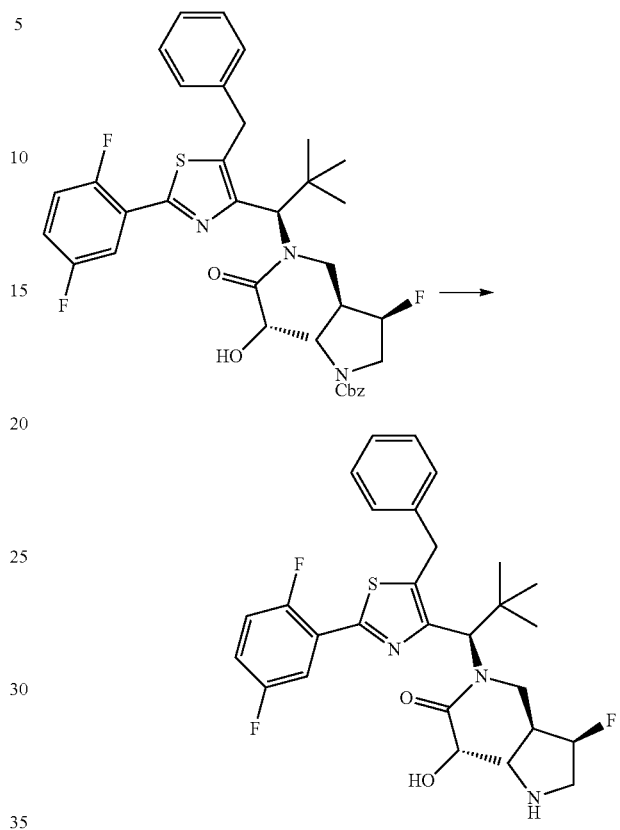

To a solution of (3R,4R)-benzyl 3-(((S)-N-((R)-1-(5-benzyl-2-(2,5-difluorophenyl)thiazol-4-yl)-2,2-dimethylpropyl)-2-hydroxypropanamido)methyl)-4-fluoropyrrolidine-1-carboxylate (108 mg, 0.159 mmol) in degassed ethanol (3 mL, 0.05 M solution) was added Pd/C (17.2 mg) under anhydrous N₂ atmosphere. After flushed with hydrogen gas, the reaction mixture equipped with a hydrogen gas balloon was stirred at room temperature for 30 min. The reaction mixture was filtered through Celite® pad that was washed with methanol and EtOAc. The volatile organic filtrate was removed in vacuo to give the crude amine, which was purified by preparative reverse phase HPLC. The combined fractions of the product were neutralized with saturated NaHCO₃ solution, which was then extracted with EtOAc. The organic layer was dried over anhydrous sodium sulfate, filtered and concentrated in vacuo. The product obtained was then dissolved in acetonitrile and water (1:1 ratio) and lyophilized for 48 h. The white powdery (S)-N-((R)-1-(5-benzyl-2-(2,5-difluorophenyl)thiazol-4-yl)-2,2-dimethylpropyl)-N-(((3S,4R)-4-fluoropyrrolidin-3-yl)methyl)-2-hydroxypropanamide was obtained in 75% yield (66 mg, over 2 steps) as the free amine. ¹H NMR (CD₃Cl, 400 MHz): δ 7.87 (1H, m), 7.33-7.27 (4H, m), 7.22-7.14 (2H, m), 7.08 (1H, m), 6.08 (1H, s), 4.71-4.62 (1H, m), 4.60-4.40 (1H, m), 4.23 (2H, s), 3.95 (1H, m), 3.63 (2H, m), 3.01-2.86 (1H, m), 2.70-2.46 (2H, m), 2.14-2.06 (2H, m), 1.45 (3H, m), 1.03 (9H, s). LC/MS (uplc): MH⁺ 546.4, 1.00 min.

Example 2

(3R,4R)-benzyl 3-(((S)-N-((R)-1-(5-benzyl-2-(2,5-difluorophenyl)thiazol-4-yl)-2,2-dimethylpropyl)tetrahydrofuran-2-carboxamido)methyl)-4-fluoropyrrolidine-1-carboxylate

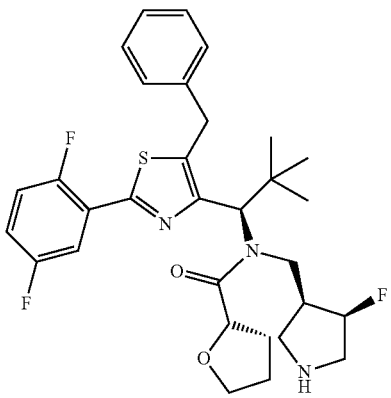

Step A: Amide Bond Formation

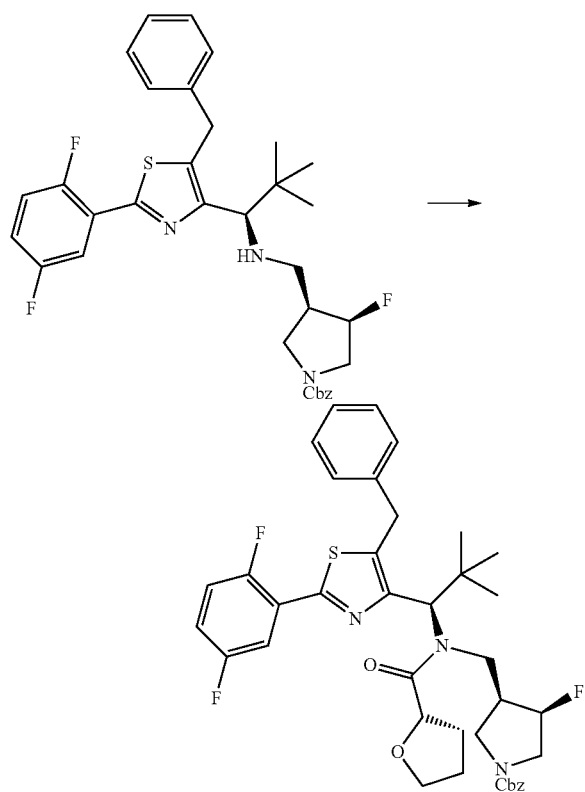

The solution of (S)-(−)-2-tetrahydrofuroic acid (50 mg, 0.43 mmol) in thionyl chloride (0.5 mL) was refluxed for 30 min, and the volatile materials were completely concentrated in vacuo. The crude product was then dissolved in dichloromethane (0.3 mL), which was then added to a solution of (3R,4R)-benzyl 3-(((R)-1-(5-benzyl-2-(2,5-difluorophenyl)thiazol-4-yl)-2,2-dimethylpropylamino)methyl)-4-fluoropyrrolidine-1-carboxylate (40 mg, 0.066 mmol) and N,N-diisopropylethylamine (34 µL, 0.197 mmol). After the reaction mixture was stirred at room temperature overnight. The reaction mixture was quenched with saturated NaHCO₃ solution and extracted with EtOAc. The organic layer was dried over anhydrous sodium sulfate, filtered, and concentrated in vacuo. The crude product was purified by preparative reverse phase HPLC. The combined fractions of the product were neutralized with saturated NaHCO₃ solution, which was then extracted with EtOAc. The organic layer was dried over anhydrous sodium sulfate, filtered, and concentrated in vacuo to yield the desired (3R,4R)-benzyl 3-(((S)-N-((R)-1-(5-benzyl-2-(2,5-difluorophenyl)thiazol-4-yl)-2,2-dimethylpropyl)tetrahydrofuran-2-carboxamido)methyl)-4-fluoropyrrolidine-1-carboxylate (30 mg, 64.6%). LC/MS (uplc): MH$^+$ 706.0, 1.40 min.

Step B: Cbz Deprotection

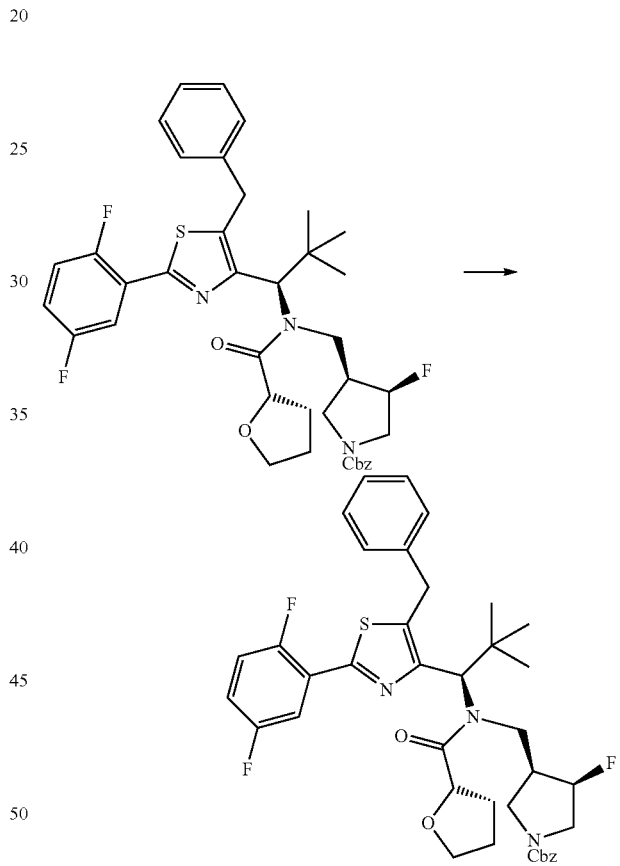

To a solution of ((3R,4R)-benzyl 3-(((S)-N-((R)-1-(5-benzyl-2-(2,5-difluorophenyl)thiazol-4-yl)-2,2-dimethylpropyl)tetrahydrofuran-2-carboxamido)methyl)-4-fluoropyrrolidine-1-carboxylate (30 mg, 0.043 mmol) in degassed ethanol (0.5 mL, 0.1 M solution) was added Pd/C (3 mg, 10 wt %) under anhydrous N₂ atmosphere. After flushed with hydrogen gas, the reaction mixture equipped with a hydrogen gas balloon was stirred at room temperature for 2 h. The reaction mixture was filtered through Celite® pad that was washed with EtOAc. The volatile organic filtrate was removed in vacuo to give the crude amine. The crude product was purified by preparative reverse phase HPLC. The combined fractions of the product were neutralized with saturated NaHCO₃ solution, which was then extracted with EtOAc (200 mL). The organic layer was dried over anhydrous sodium sulfate, filtered and concentrated in vacuo. The dried product was then dissolved in acetonitrile and water (1:1 ratio) and lyophilized for 48 h The white powdery (S)-N-((R)-1-(5-benzyl-2-(2,5-difluorophenyl)thiazol-4-yl)-2,2-dimethylpropyl)-N-(((3S,4R)-4-fluoropyrrolidin-3-yl)methyl)tetrahydrofuran-2-carboxamide was obtained in 14% (5.4 mg) as the free amine. LC/MS (uplc): MH$^+$ 572.0, 1.04 min.

Example 3

2-(((R)-1-(2-benzyl-5-(2,5-difluorophenyl)thiophen-3-yl)-2,2-dimethylpropyl)((S)-3-(1,3-dioxoisoindolin-2-yl)-4-fluorobutyl)amino)-2-oxoethyl acetate

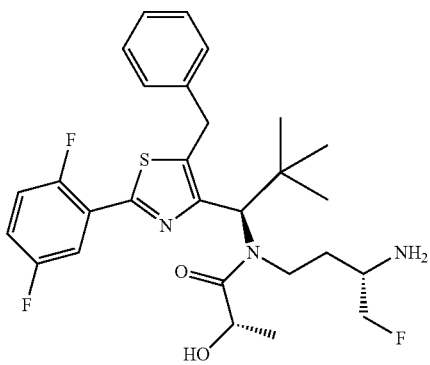 [SMILES: C[C@H](O)C(=O)N(CC[C@H](N)CF)[C@@H](c1nc(-c2cc(F)ccc2F)sc1Cc1ccccc1)C(C)(C)C]

Step A: Reductive Amination

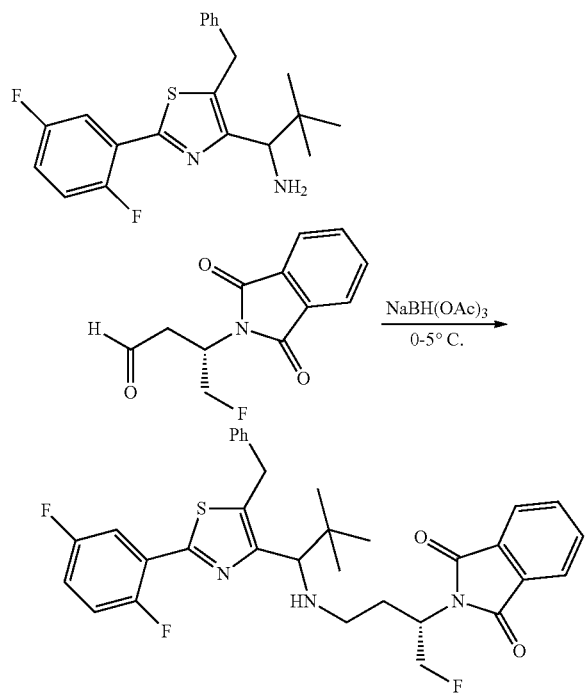

To a solution of 1-(5-benzyl-2-(2,5-difluorophenyl)thiazol-4-yl)-2,2-dimethylpropan-1-amine (95 mg, 0.267 mmol) in dichloromethane (2 mL) was added (S)-3-(1,3-dioxoisoindolin-2-yl)-4-fluorobutanal (62.8 mg 0.267 mmol) at 0° C. followed by addition of Na(OAc)$_3$BH (169.8 mg, 0.801 mmol). The reaction mixture was stirred at this temperature under nitrogen for 1 h, quenched with saturated NaHCO3 solution, and then extracted by EtOAc. The organic layer was washed with water and brine, dried over anhydrous Na2SO4, filtered, and concentrated. The crude product was purified by flash chromatography (30% EtOAc in Hexanes) to yield a diastereomeric mixture of 2-((2S)-4-(1-(5-benzyl-2-(2,5-difluorophenyl)thiazol-4-yl)-2,2-dimethylpropylamino)-1-fluorobutan-2-yl)isoindoline-1,3-dione as a white foam (65 mg, 41%). LC/MS (uplc): MH+ 592.1, 1.05 min and 1.07 min.

Step B: Amide Bond Formation

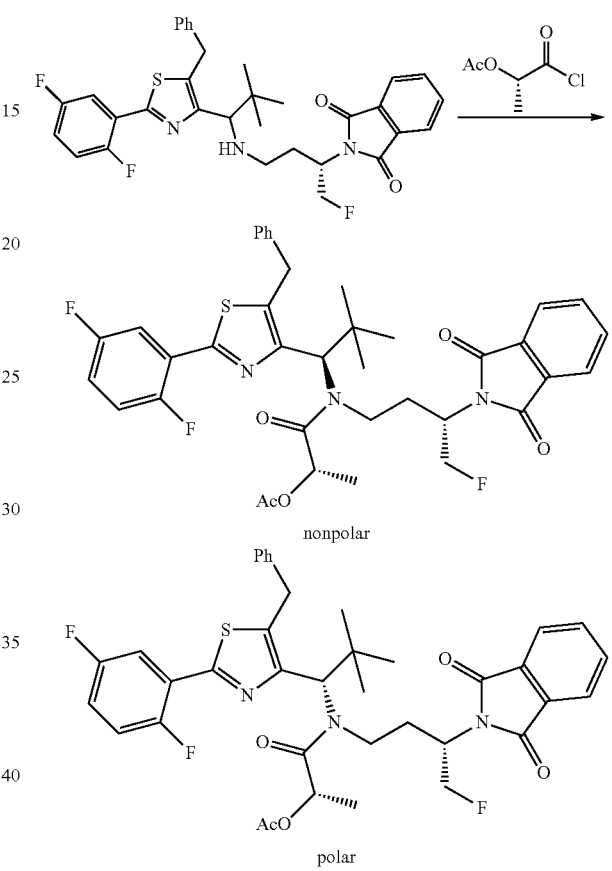

To a solution of 2-((2S)-4-(1-(5-benzyl-2-(2,5-difluorophenyl)thiazol-4-yl)-2,2-dimethylpropylamino)-1-fluorobutan-2-yl)isoindoline-1,3-dione (65 mg, 0.125 mmol) in dichloromethane (1 mL, 0.1 M solution) at room temperature was added DIEA (65.3 μL, 0.375 mmol). (S)-1-Chloro-1-oxopropan-2-yl acetate (35 μL, 0.276 mmol) was then added dropwise over 2 min. The resulting solution was stirred at room temperature for 1.5 h. The reaction mixture was quenched with saturated NaHCO$_3$ solution and extracted with EtOAc. The organic layer was dried over anhydrous sodium sulfate and filtered. After the volatile organic materials were removed in vacuo, the crude diastereomers were purified by preparative reverse phase HPLC. The combined fractions of each diastereomer were neutralized with saturated NaHCO$_3$ solution, which was then extracted with EtOAc. The organic layer was dried over anhydrous sodium sulfate, filtered and concentrated in vacuo. The nonpolar diastereomer, (R)-1-(((R)-1-(5-benzyl-2-(2,5-difluorophenyl)thiazol-4-yl)-2,2-dimethylpropyl)((S)-3-(1,3-dioxoisoindolin-2-yl)-4-fluorobutyl)amino)-1-oxopropan-2-yl acetate, was obtained in 23% (10 mg). LC/MS (uplc) MH+ 706.2, 1.37 min. The polar isomer, (R)-1-(((S)-1-(5-benzyl-2-(2,5-difluorophenyl)thiazol-4-yl)-2,2-dimethylpropyl)((S)-3-(1,3-dioxoisoindolin-2-yl)-4-fluorobutyl)amino)-1-oxopropan-2-yl acetate, was obtained in 12% (5 mg). LC/MS (uplc) MH+ 706.2, 1.36 min.

Step C: Deprotection

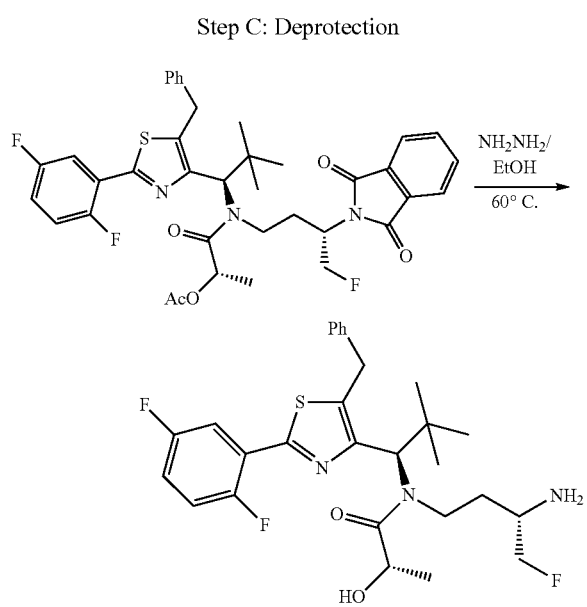

To a solution of (R)-1-(((R)-1-(5-benzyl-2-(2,5-difluorophenyl)thiazol-4-yl)-2,2-dimethylpropyl)((S)-3-(1,3-dioxoisoindolin-2-yl)-4-fluorobutyl)amino)-1-oxopropan-2-yl acetate (10 mg, 0.014 mmol) in EtOH (1 mL) was added anhydrous hydrazine (45 µL). The reaction was heated at 60° C. for 14 h. After cooled the reaction mixture, the white precipitate was filtered through Celite® pad with EtOH washes. The filtrate was concentrated and purified by preparative reverse phase HPLC. The pure fractions were combined and lyophilized to yield (S)-N-((S)-3-amino-4-fluorobutyl)-N-((R)-1-(5-benzyl-2-(2,5-difluorophenyl)thiazol-4-yl)-2,2-dimethylpropyl)-2-hydroxypropanamide (2.3 mg, 25%) as TFA salt. LC/MS (uplc) MH+ 543.2, 1.05 min.

Example 4

((S)-N-((R)-1-(5-benzyl-2-(2,5-difluorophenyl)oxazol-4-yl)-2,2-dimethylpropyl)-N-(((3S,4R)-4-fluoropyrrolidin-3-yl)methyl)-2-hydroxypropanamide

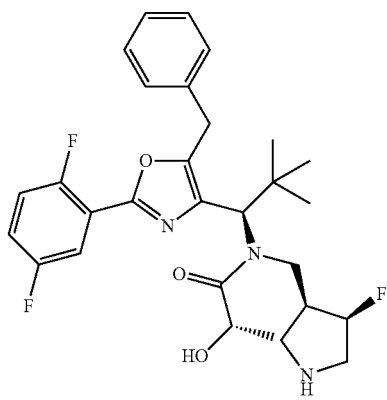 [SMILES: C[C@H](O)C(=O)N(C[C@@H]1CNC[C@@H]1F)[C@@H](c1nc(-c2cc(F)ccc2F)oc1Cc1ccccc1)C(C)(C)C]

Step A: Synthesis of Oxzole Core

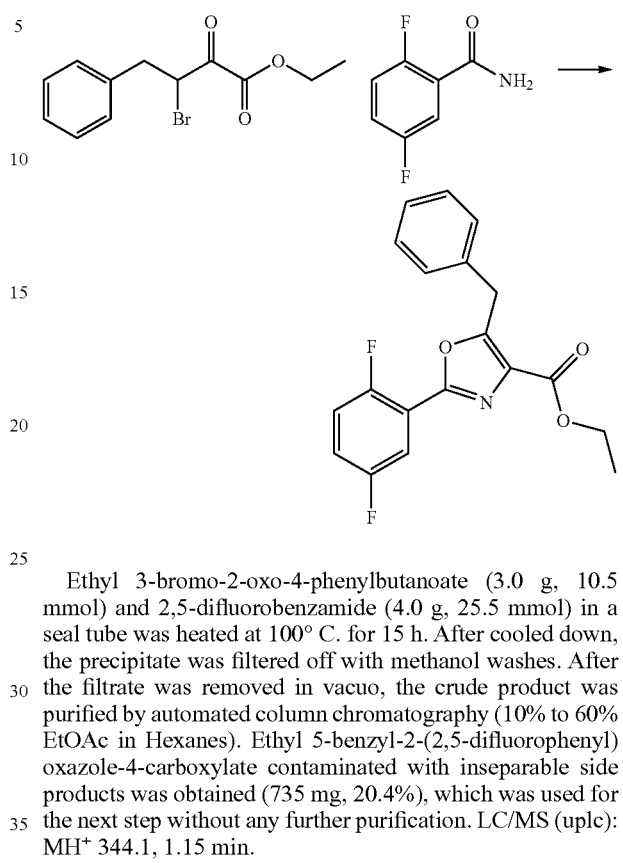

Ethyl 3-bromo-2-oxo-4-phenylbutanoate (3.0 g, 10.5 mmol) and 2,5-difluorobenzamide (4.0 g, 25.5 mmol) in a seal tube was heated at 100° C. for 15 h. After cooled down, the precipitate was filtered off with methanol washes. After the filtrate was removed in vacuo, the crude product was purified by automated column chromatography (10% to 60% EtOAc in Hexanes). Ethyl 5-benzyl-2-(2,5-difluorophenyl)oxazole-4-carboxylate contaminated with inseparable side products was obtained (735 mg, 20.4%), which was used for the next step without any further purification. LC/MS (uplc): MH+ 344.1, 1.15 min.

Step B: Reduction of Oxazole Esters

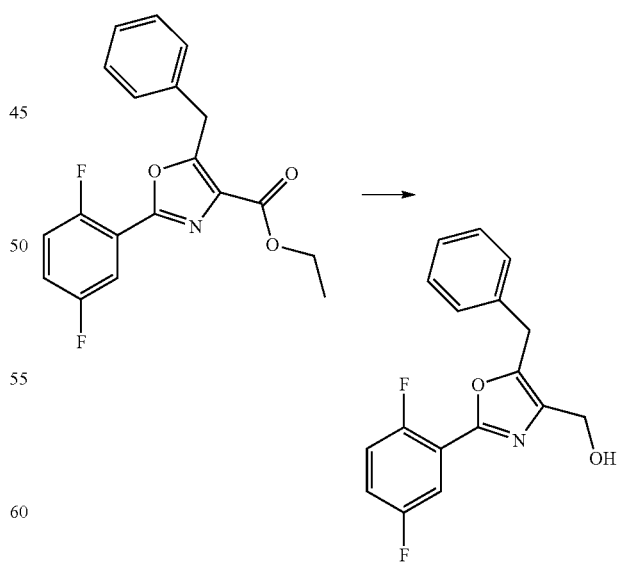

To a solution of ethyl 5-benzyl-2-(2,5-difluorophenyl)oxazole-4-carboxylate (590 mg, 1.72 mmol) in THF (8.6 mL) was slowly added LiBH4 (56.2 mg, 2.58 mmol) at room temperature. The reaction mixture was stirred for overnight.

After quenched with water, the reaction mixture was extracted with EtOAc. The organic layers was washed with saturated NaHCO3 solution and brine, dried over anhydrous Na2SO4, filtered, and concentrated. The crude product was purified by automatic column chromatography (0 to 100% EtOAc in Hexanes) to yield (5-benzyl-2-(2,5-difluorophenyl)oxazol-4-yl)methanol (460 mg, 88%) as a white solid. LC/MS (uplc): MH+ 302.2, 0.92 min.

Step C: Oxidation of Oxazole Alcohol

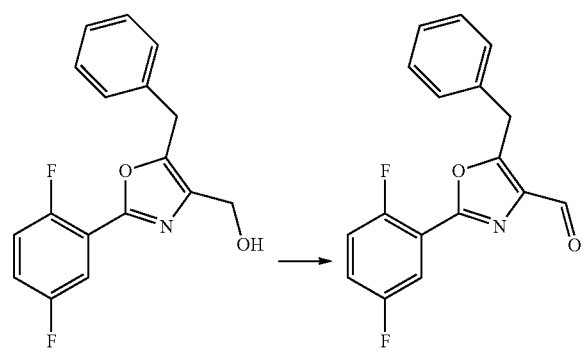 [SMILES: OCc1nc(-c2cc(F)ccc2F)oc1Cc1ccccc1 ; O=Cc1nc(-c2cc(F)ccc2F)oc1Cc1ccccc1]

To a solution of (5-benzyl-2-(2,5-difluorophenyl)oxazol-4-yl)methanol (966 mg, 3.21 mmol) in dichloromethane (16 mL) was added Dess-Martin periodinane (2.04 mg, 4.81 mmol). The reaction mixture was stirred at room temperature for overnight. 20 mL of saturated NaHCO$_3$ solution and saturated Na$_2$S$_2$O$_3$ solution (8:1) was added for quenching the reaction. After stirred for 1 h, the reaction mixture was extracted by EtOAc. The organic layers was washed with water and brine, dried over anhydrous Na$_2$SO$_4$, filtered, and concentrated. The crude product was purified by automatic column chromatography to yield 5-benzyl-2-(2,5-difluorophenyl)oxazole-4-carbaldehyde (898 mg, 94%) as white solid. $^1$H NMR (CD$_3$Cl, 400 MHz): δ 10.0 (1H, s), 7.70 (1H, m), 7.37-7.31 (3H, m), 7.29-7.25 (2H, m), 7.19-7.14 (2H, m), 4.44 (2H, s). LC/MS (uplc): 300.0, 1.06 min.

Step D: Synthesis of t-Butyl Sulfinimine

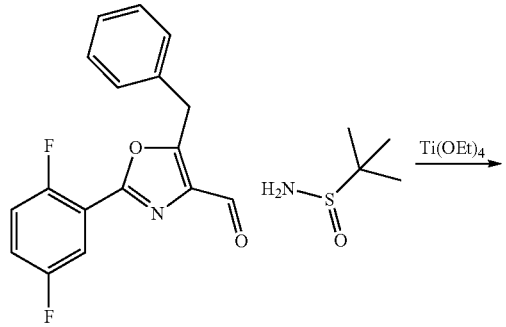

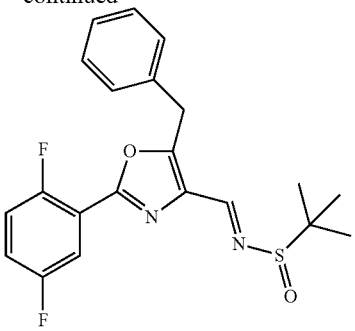

To a solution of 5-benzyl-2-(2,5-difluorophenyl)oxazole-4-carbaldehyde (898 mg, 3.0 mmol) in THF (30.0 mL) was added (±)-2-methylpropane-2-sulfinamide (364 mg, 3.0 mmol), and Ti(OEt)$_4$ (1.37 mL, 6.6 mmol). The reaction mixture was stirred for 4 h at room temperature. The reaction mixture was diluted with brine (30 mL) and EtOAc (60 mL) followed by addition of Celite®. Then, the mixture was vigorously stirred for 1 h, and filtered. The filtrate was extracted by EtOAc. The organic layers was washed with water and brine, dried over anhydrous Na$_2$SO$_4$, filtered, and concentrated. The crude product (770 mg, 64%) was purified by automatic column chromatography to yield (±)—N-((5-benzyl-2-(2,5-difluorophenyl)oxazol-4-yl)methylene)-2-methylpropane-2-sulfinamide as pale yellow solid. LC/MS (uplc): MH+ 403.0, 1.21 min.

Step E: t-Butyl Lithium Addition Reaction

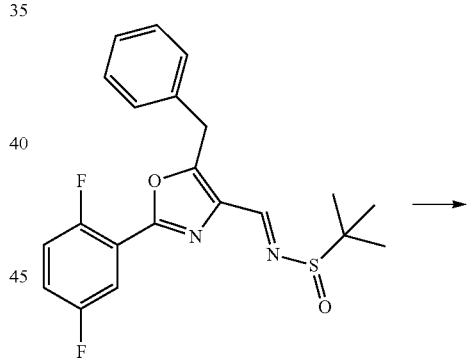

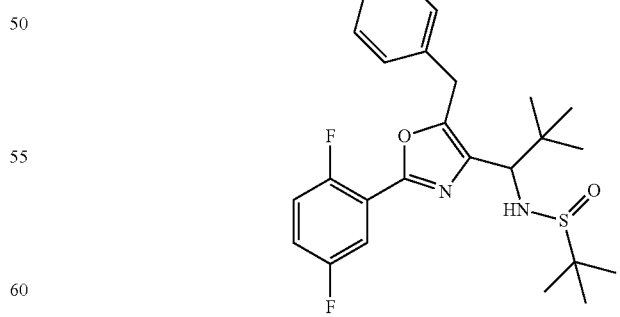

To a solution of (±)-N-((5-benzyl-2-(2,5-difluorophenyl)oxazol-4-yl)methylene)-2-methylpropane-2-sulfinamide (770 mg, 1.91 mmol) in anhydrous THF (7.6 mL) was slowly added $^t$BuLi (1.7 M solution in pentane, 3.34 mL, 5.74 mmol) at −78° C. After the reaction mixture was stirred at −78° C. for 3 h, the reaction was quenched with MeOH (2 mL) followed by addition of saturated NH₄Cl solution (10 mL). Upon warming up to room temperature, the reaction mixture was stirred for 30 min and then extracted with EtOAc (50 mL). The organic layer was washed with water and brine, dried over anhydrous Na₂SO₄, filtered, and concentrated. The crude product was purified by automatic column chromatography to yield (±)-N-(1-(5-benzyl-2-(2,5-difluorophenyl)oxazol-4-yl)-2,2-dimethylpropyl)-2-methylpropane-2-sulfinamide (340 mg, 38.6%) as a pale yellow solid. ¹H NMR (CDCl₃, 400 MHz): δ 7.64 (1H, m), 7.38-7.27 (4H, m), 7.27-7.21 (1H, m), 7.12-6.99 (2H, m), 4.24 (1H, m), 4.12 (2Hm), 3.92 (1H, m), 1.27 (9H, s), 0.95 (9H, s). LC/MS (uplc): MH⁺ 461.2, 1.34 min.

Step F: Deprotection of t-Butyl Sulfinyl Group

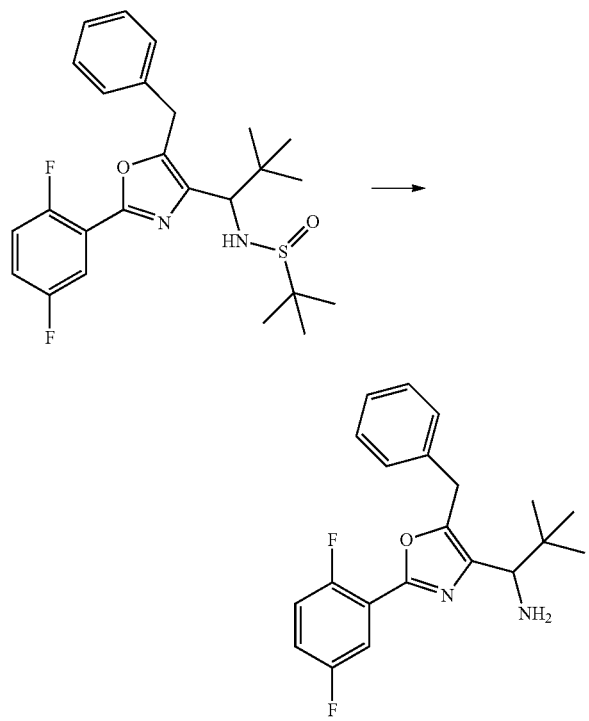

To a solution of (±)-N-(1-(5-benzyl-2-(2,5-difluorophenyl)oxazol-4-yl)-2,2-dimethylpropyl)-2-methylpropane-2-sulfinamide (340 mg, 0.738 mmol) in MeOH (10 mL) was added 4 M HCl in dioxane (369 µL, 1.476 mmol). The reaction mixture was stirred at room temperature for 1 h. After quenched with saturated NaHCO₃ solution and diluted with EtOAc, the reaction mixture was stirred for 15 min and extracted with EtOAc. The organic layer was washed with water and brine, dried over anhydrous Na₂SO₄, filtered, and concentrated. The crude (±)-1-(5-benzyl-2-(2,5-difluorophenyl)oxazol-4-yl)-2,2-dimethylpropan-1-amine was obtained in 91% yield (240 mg), which was used for the next step without further purification (a major side product, methyl 2-methylpropane-2-sulfinate, was completely removed under high vacuum). LC/MS (uplc): MH⁺ 340.2 (—NH₂), 0.91 min.

Step G: Reductive Amination

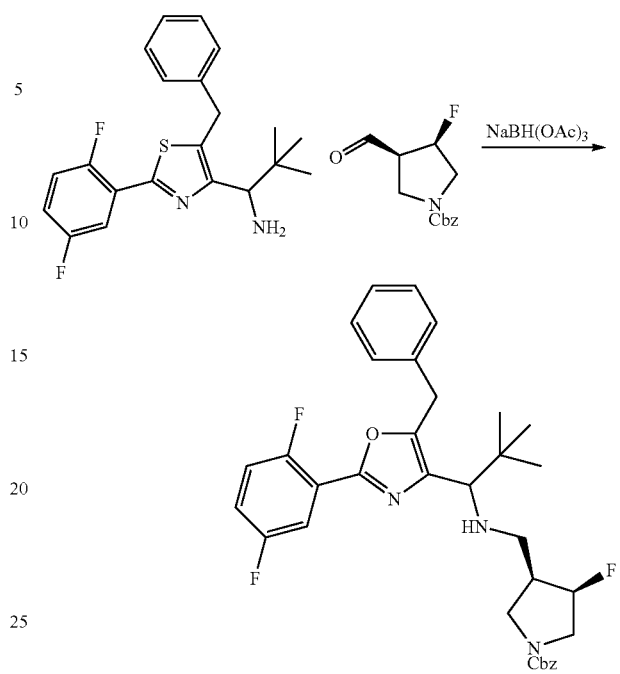

To a solution of (±)-1-(5-benzyl-2-(2,5-difluorophenyl)oxazol-4-yl)-2,2-dimethylpropan-1-amine (240 mg, 0.673 mmol) in CH₂Cl₂ (5.0 mL) was added NaBH(OAc)₃ (2.86 g, 13.5 mmol). To this solution, the crude (3R,4S)-benzyl 3-fluoro-4-formylpyrrolidine-1-carboxylate (obtained from 2.0 equiv. of (3R,4R)-benzyl 3-fluoro-4-vinylpyrrolidine-1-carboxylate) in CH₂Cl₂ (1.0 mL) was rapidly added at room temperature. After stirred for 20 min, the reaction mixture was quenched with saturated NaHCO₃ solution and extracted with EtOAc. The organic layer was washed with water and brine, dried over anhydrous Na₂SO₄, filtered and concentrated. The crude product was purified on preparative reverse phase HPLC. The combined fractions of the product were neutralized with saturated NaHCO₃ solution, which was then extracted with EtOAc. The organic layer was dried over anhydrous sodium sulfate, filtered and concentrated in vacuo to yield (±)-(3R,4R)-benzyl 3-((1-(5-benzyl-2-(2,5-difluorophenyl)oxazol-4-yl)-2,2-dimethylpropylamino)methyl)-4-fluoropyrrolidine-1-carboxylate (37 mg, 9.2%). LC/MS (uplc) MH⁺ 592.4, 0.91 min.

Step H: Amide Bond Formation

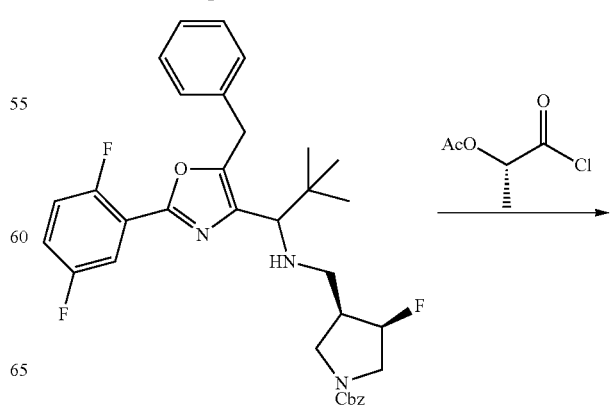

-continued

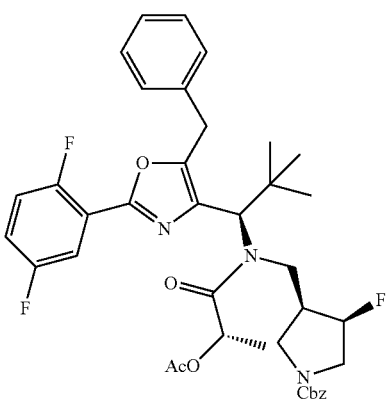

To a solution of (±)-(3R,4R)-benzyl 3-((1-(5-benzyl-2-(2,5-difluorophenyl)oxazol-4-yl)-2,2-dimethylpropylamino)methyl)-4-fluoropyrrolidine-1-carboxylate (37 mg, 0.063 mmol) in dichloromethane (0.63 mL, 0.1 M solution) at room temperature was added N,N-diisopropylethylamine (55 µL, 0.313 mmol). (S)-1-Chloro-1-oxopropan-2-yl acetate (15.8 µL, 0.125 mmol) was then added dropwise over 2 min. The resulting solution was stirred at room temperature for 2 h. The reaction mixture was quenched with saturated NaHCO$_3$ solution and extracted with EtOAc. The organic layer was washed with water and brine, dried over anhydrous sodium sulfate, filtered, and concentrated in vacuo. Two diastereomers were separated on preparative TLC (2% MeOH in dichloromethane). The polar diastereomer, (3R,4R)-benzyl 3-(((S)-2-acetoxy-N-((R)-1-(5-benzyl-2-(2,5-difluorophenyl)oxazol-4-yl)-2,2-dimethylpropyl)propanamido)methyl)-4-fluoropyrrolidine-1-carboxylate, was obtained in 17% yield (7.5 mg). LC/MS (uplc): MH+ 706.4, 1.34 min. The nonpolar diastereomer, (3R,4R)-benzyl 3-(((S)-2-acetoxy-N—((S)-1-(5-benzyl-2-(2,5-difluorophenyl)oxazol-4-yl)-2,2-dimethylpropyl)propanamido)methyl)-4-fluoropyrrolidine-1-carboxylate, was obtained in 16% yield (7.0 mg). LC/MS (uplc): MH+ 706.4, 1.35 min.

Step I: Deacetylation

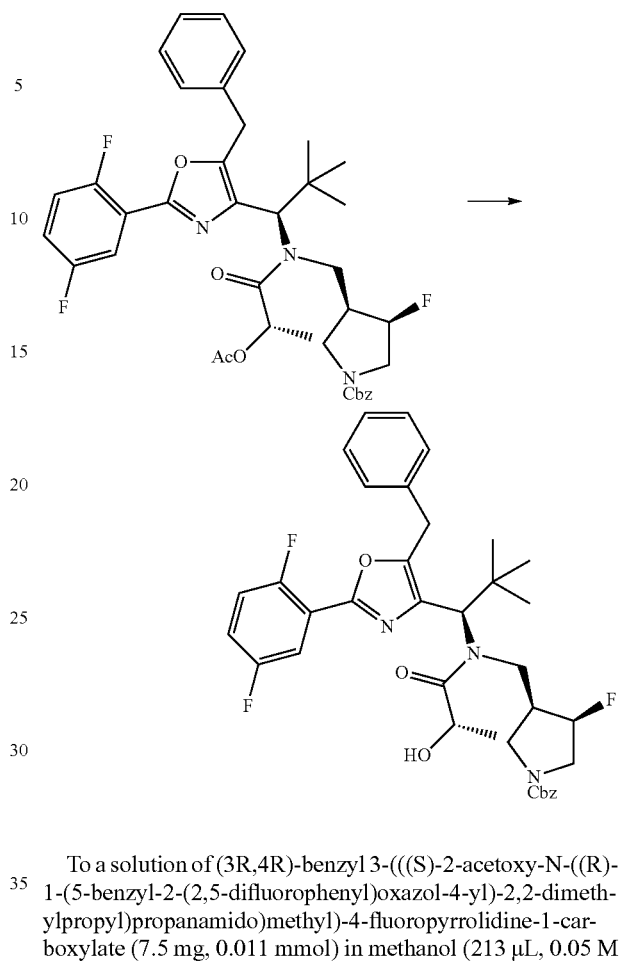

To a solution of (3R,4R)-benzyl 3-(((S)-2-acetoxy-N-((R)-1-(5-benzyl-2-(2,5-difluorophenyl)oxazol-4-yl)-2,2-dimethylpropyl)propanamido)methyl)-4-fluoropyrrolidine-1-carboxylate (7.5 mg, 0.011 mmol) in methanol (213 µL, 0.05 M solution) was added K$_2$CO$_3$ (14.69 mg, 0.106 mmol) at room temperature. After stirred for 30 min, the reaction mixture was quenched with water and then extracted with EtOAc. The organic layer was washed with water and brine, dried over anhydrous sodium sulfate, filtered, and concentrated in vacuo. The crude (3R,4R)-benzyl 3-(((S)-N-((R)-1-(5-benzyl-2-(2,5-difluorophenyl)oxazol-4-yl)-2,2-dimethylpropyl)-2-hydroxypropanamido)methyl)-4-fluoropyrrolidine-1-carboxylate (6.5 mg, 92%) was used for the next step with further purification. LC/MS (uplc): MH+ 664.3, 1.30 min.

Step J: Cbz Deprotection

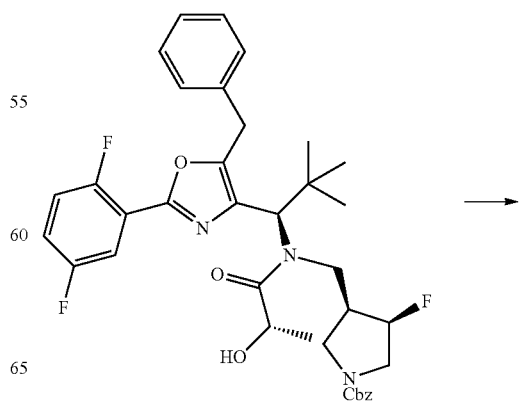

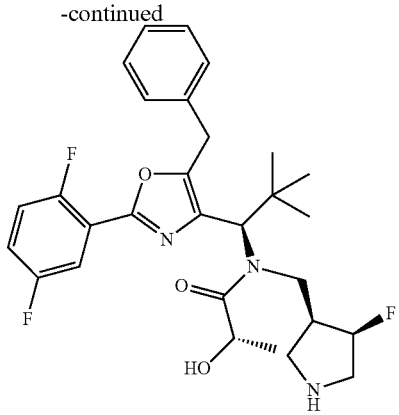

To a solution of (3R,4R)-benzyl 3-(((S)-N-((R)-1-(5-benzyl-2-(2,5-difluorophenyl)oxazol-4-yl)-2,2-dimethylpropyl)-2-hydroxypropanamido)methyl)-4-fluoropyrrolidine-1-carboxylate (6.5 mg, 0.8 μmol) in degassed ethanol (980 μL, 0.01 M solution) was added Pd/C (5.0 mg) under anhydrous $N_2$ atmosphere. After flushed with hydrogen gas, the reaction mixture equipped with a hydrogen gas balloon was stirred at room temperature for 30 min. The reaction mixture was filtered through Celite® pad that was washed with methanol and EtOAc. The volatile organic filtrate was removed in vacuo to give the crude amine, which was purified by preparative reverse phase HPLC. The combined fractions of the product were neutralized with saturated $NaHCO_3$ solution, which was then extracted with EtOAc. The organic layer was dried over anhydrous sodium sulfate, filtered and concentrated in vacuo. The crude product was purified by preparative TLC to yield (S)-N-((R)-1-(5-benzyl-2-(2,5-difluorophenyl)oxazol-4-yl)-2,2-dimethylpropyl)-N-(((3S,4R)-4-fluoropyrrolidin-3-yl)methyl)-2-hydroxypropanamide (2.5 mg, 48.2%) as the free amine. LC/MS (uplc): $MH^+$ 530.3, 0.94 min.

Example 5

(S)-N-((S)-3-amino-4-fluorobutyl)-N-((R)-1-(5-benzyl-2-(2,5-difluorophenyl)oxazol-4-yl)-2,2-dimethylpropyl)-2-hydroxypropanamide

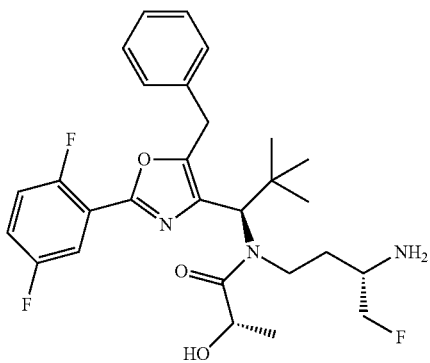 [SMILES: C[C@H](O)C(=O)N(CC[C@H](N)CF)[C@@H](c1nc(-c2cc(F)ccc2F)oc1Cc1ccccc1)C(C)(C)C]

Step A: Reductive Amination

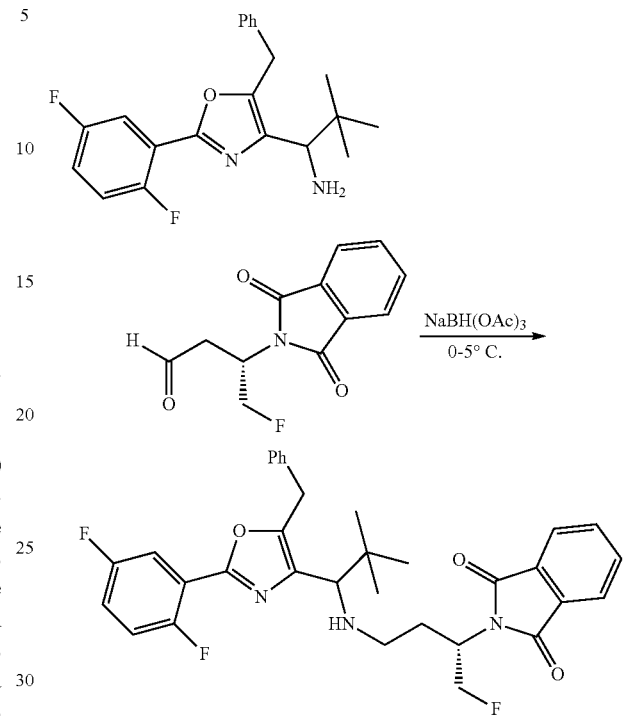

To a solution of (±)-1-(5-benzyl-2-(2,5-difluorophenyl)oxazol-4-yl)-2,2-dimethylpropan-1-amine (25 mg, 0.07 mmol) in dichloromethane (0.5 mL) was added (S)-3-(1,3-dioxoisoindolin-2-yl)-4-fluorobutanal (16.5 mg 0.07 mmol) at 0° C. followed by addition of $Na(OAc)_3BH$ (22 mg, 0.11 mmol). The reaction mixture was stirred at this temperature under nitrogen for 1 h, quenched with saturated $NaHCO_3$ solution, and then extracted by EtOAc. The organic layer was washed with water and brine, dried over anhydrous $Na_2SO_4$, filtered, and concentrated. The crude products, (±)-2-((2S)-4-(1-(5-benzyl-2-(2,5-difluorophenyl)oxazol-4-yl)-2,2-dimethylpropylamino)-1-fluorobutan-2-yl)isoindoline-1,3-dione, were obtained as a diastereomeric mixture of (±)-2-((2S)-4-(1-(5-benzyl-2-(2,5-difluorophenyl)thiazol-4-yl)-2,2-dimethylpropylamino)-1-fluorobutan-2-yl)isoindoline-1,3-dione (39 mg, 97%). LC/MS (uplc): $MH^+$ 576.4, 1.03 min and 1.05 min.

Step B: Amide Bond Formation

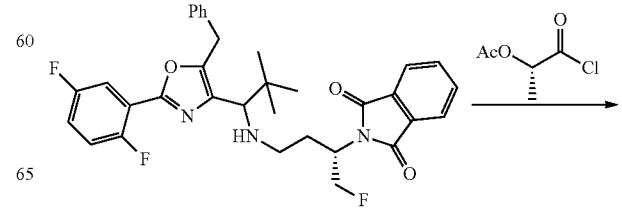

-continued

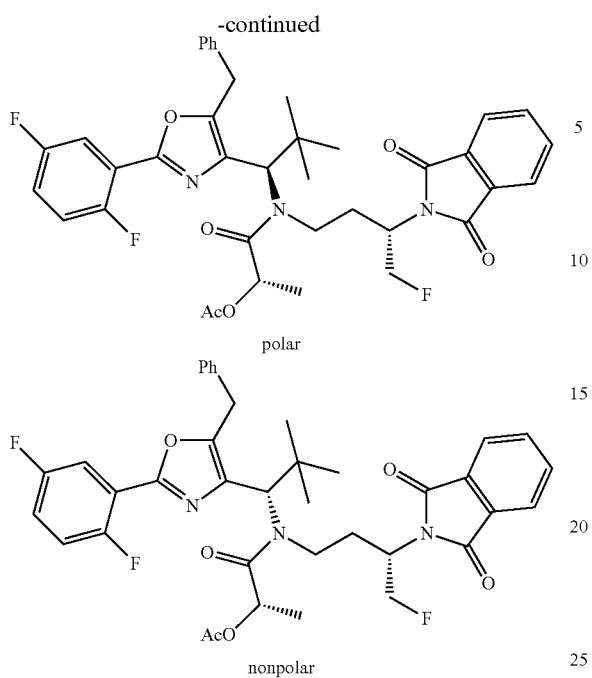

polar nonpolar

To a solution of crude (±)-2-((2S)-4-(1-(5-benzyl-2-(2,5-difluorophenyl)thiazol-4-yl)-2,2-dimethylpropylamino)-1-fluorobutan-2-yl)isoindoline-1,3-dione (39 mg, 0.068 mmol) in dichloromethane (0.5 mL) at room temperature was added DIEA (52 µL, 0.29 mmol). (S)-1-Chloro-1-oxopropan-2-yl acetate (28 µL, 0.22 mmol) was then added dropwise over 2 min. The resulting solution was stirred at room temperature for 1.5 h. The reaction mixture was quenched with saturated NaHCO₃ solution and extracted with EtOAc. The organic layer was dried over anhydrous sodium sulfate and filtered. After the volatile organic materials were removed in vacuo, the crude diastereomers were purified by preparative TLC. The polar compound on TLC, (S)-1-(((R)-1-(5-benzyl-2-(2,5-difluorophenyl)oxazol-4-yl)-2,2-dimethylpropyl)((S)-3-(1,3-dioxoisoindolin-2-yl)-4-fluorobutyl)amino)-1-oxopropan-2-yl acetate, was obtained in 17% (8 mg). LC/MS (uplc) MH+ 690.3, 1.27 min. The nonpolar one, (S)-1-(((S)-1-(5-benzyl-2-(2,5-difluorophenyl)oxazol-4-yl)-2,2-dimethyl propyl)((S)-3-(1,3-dioxoisoindolin-2-yl)-4-fluorobutyl)amino)-1-oxopropan-2-yl acetate, was obtained in 17% (8 mg). LC/MS (uplc) MH+ 690.3, 1.28 min.

Step C: Deprotection

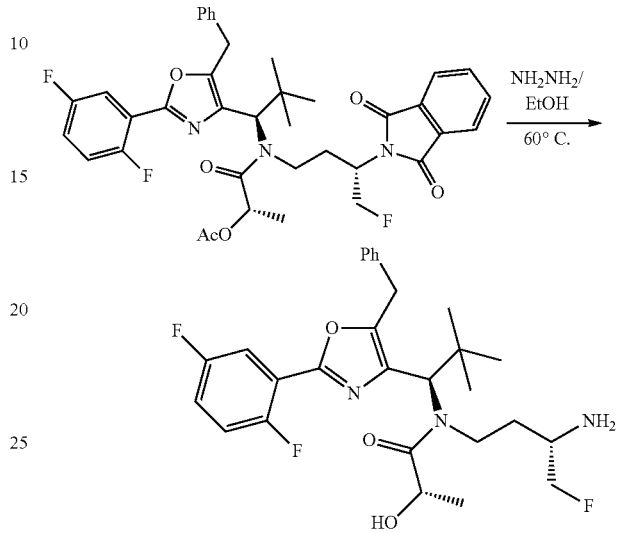

To a solution of (R)-1-(((R)-1-(5-benzyl-2-(2,5-difluorophenyl)thiazol-4-yl)-2,2-dimethylpropyl)((S)-3-(1,3-dioxoisoindolin-2-yl)-4-fluorobutyl)amino)-1-oxopropan-2-yl acetate (8 mg, 0.012 mmol) in EtOH (1 mL) was added anhydrous hydrazine (40 µL). The reaction was heated at 50° C. for 24 h. After cooled the reaction mixture, the white precipitate was filtered through Celite® pad with EtOH washes. The filtrate was concentrated and purified by preparative reverse phase HPLC. The pure fractions were combined and lyophilized to yield (S)-N-((S)-3-amino-4-fluorobutyl)-N-((R)-1-(5-benzyl-2-(2,5-difluorophenyl)oxazol-4-yl)-2,2-dimethylpropyl)-2-hydroxypropanamide (3.2 mg) as TFA salt. LC/MS (uplc) MH+ 518.2, 0.96 min.

Examples 6, 7, and 8 were prepared using the procedure outlined for Examples 4, 5, and 3 respectively.

TABLE 1

| Compound | Structure | MH+ | Name | Synthetic Method |
|---|---|---|---|---|
| 6 | 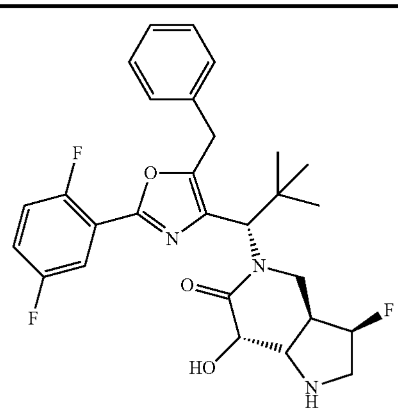 | 530.4 | (S)-N-((S)-1-(5-benzyl-2-(2,5-difluorophenyl)oxazol-4-yl)-2,2-dimethylpropyl)-N-(((3S,4R)-4-fluoropyrrolidin-3-yl)methyl)-2-hydroxypropanamide | Example 4 |

TABLE 1-continued

| Compound | Structure | MH+ | Name | Synthetic Method |
|---|---|---|---|---|
| 7 | 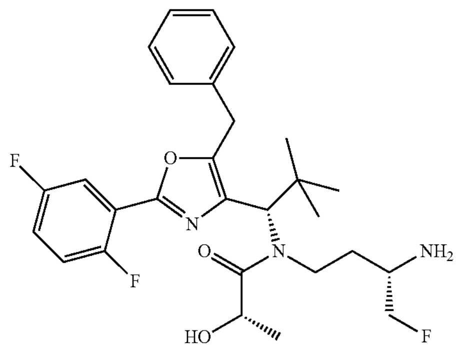 [SMILES: C[C@H](O)C(=O)N(CC[C@H](N)CF)[C@H](c1nc(-c2cc(F)ccc2F)oc1Cc1ccccc1)C(C)(C)C] | 518.2 | (S)-N-((S)-3-amino-4-fluorobutyl)-N-((S)-1-(5-benzyl-2-(2,5-difluorophenyl)oxazol-4-yl)-2,2-dimethylpropyl)-2-hydroxypropanamide | Example 5 |
| 8 | 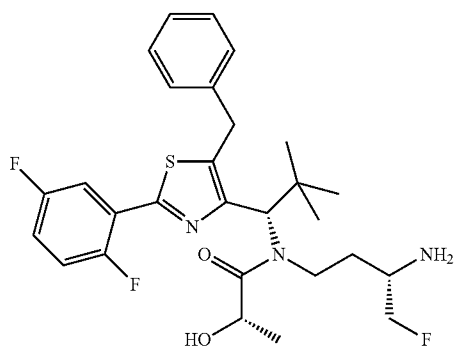 [SMILES: C[C@H](O)C(=O)N(CC[C@H](N)CF)[C@H](c1nc(-c2cc(F)ccc2F)sc1Cc1ccccc1)C(C)(C)C] | 543.2 | (S)-N-((S)-3-amino-4-fluorobutyl)-N-((S)-1-(5-benzyl-2-(2,5-difluorophenyl)thiazol-4-yl)-2,2-dimethylpropyl)-2-hydroxypropanamide | Example 3 |

Example 9

Assay for Determining KSP Activity

This example provides a representative in vitro assay for determining KSP activity in vitro. Purified microtubules obtained from bovine brain were purchased from Cytoskeleton Inc. (Denver, Colo., USA). The motor domain of human KSP (Eg 5, KNSL1) was cloned, expressed, and purified to greater than 95% homogeneity. Biomol Green was purchased from Affinity Research Products Ltd. (Matford Court, Exeter, Devon, United Kingdom). Microtubules and KSP motor protein (i.e., the KSP motor domain) were diluted in assay buffer (20 mM Tris-HCl (pH 7.5), 1 mM MgCl$_2$, 10 mM DTT and 0.25 mg/mL BSA) to a final concentration of 35 μg/mL microtubules and 45 nM KSP. The microtubule/KSP mixture was then pre-incubated at 37° C. for 10 min to promote the binding of KSP to microtubules.

To each well of the testing plate (384-well plate) containing 1.25 μL of inhibitor or test compound in DMSO (or DMSO only in the case of controls) were added 25 μL of ATP solution (ATP diluted to a concentration of 300 μM in assay buffer) and 25 μL of the above-described microtubule/KSP solution. The plates were incubated at RT for 1 hour. Following incubation, 65 μL of Biomol Green (a malachite green-based dye that detects the release of inorganic phosphate) was added to each well. The plates were incubated for an additional 5-10 minutes then the absorbance at 630 nm was determined using a Victor II plate reader. The amount of absorbance at 630 nm corresponded to the amount of KSP activity in the samples. The IC$_{50}$ of each inhibitor or test compound was then determined based on the decrease in absorbance at 630 nm at each concentration, via nonlinear regression using either XLFit for Excel or Prism data analysis software by GraphPad Software Inc.

Outlined in Table 2 are IC$_{50}$ values for representative compounds from the present invention.

TABLE 2
| Example # | STRUCTURE | Biological Activity (IC50/GI50) |
|---|---|---|
| 1 | 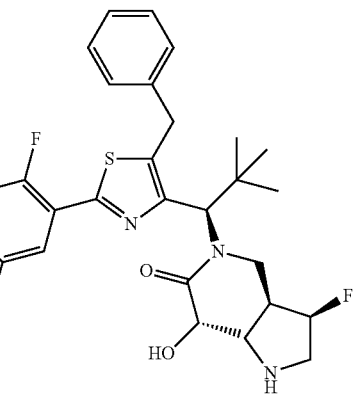 | 0.84 nM/0.18 nM |
| 2 | 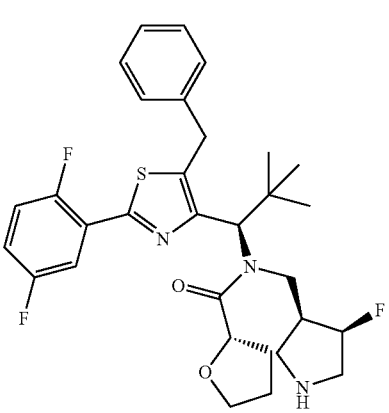 [SMILES: CC(C)(C)[C@H](c1nc(-c2cc(F)ccc2F)sc1Cc1ccccc1)N(C[C@@H]1CNC[C@@H]1F)C(=O)[C@@H]1CCCO1] | 10.0 nM/1.4 nM |
| 3 | 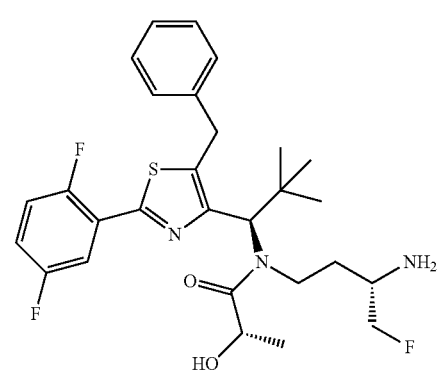 | 2.6 nM/2.2 nM |
| 4 | 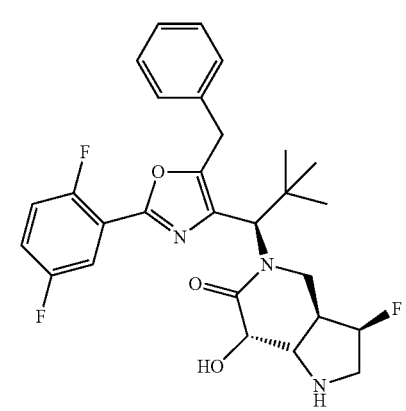 [SMILES: C[C@H](O)C(=O)N(C[C@@H]1CNC[C@@H]1F)[C@@H](c1nc(-c2cc(F)ccc2F)oc1Cc1ccccc1)C(C)(C)C] | 7.18 nM/3.5 nM |

TABLE 2-continued

| Example # | STRUCTURE | Biological Activity (IC50/GI50) |
|---|---|---|
| 5 | 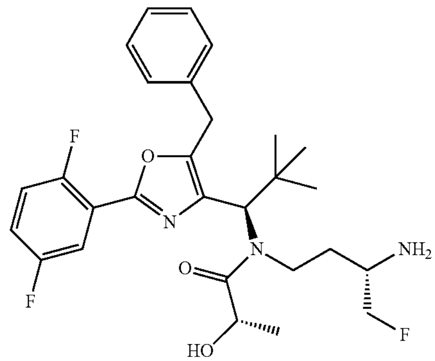 [SMILES: C[C@H](O)C(=O)N(CC[C@H](N)CF)[C@@H](c1nc(-c2cc(F)ccc2F)oc1Cc1ccccc1)C(C)(C)C] | 2.54 nM/4.82 nM |
| 6 | 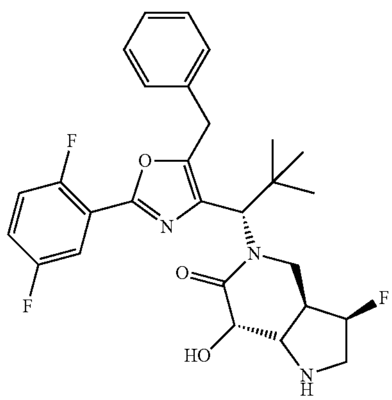 [SMILES: C[C@H](O)C(=O)N(C[C@@H]1CNC[C@@H]1F)[C@H](c1nc(-c2cc(F)ccc2F)oc1Cc1ccccc1)C(C)(C)C] | 1000 nM/N/A |
| 7 | 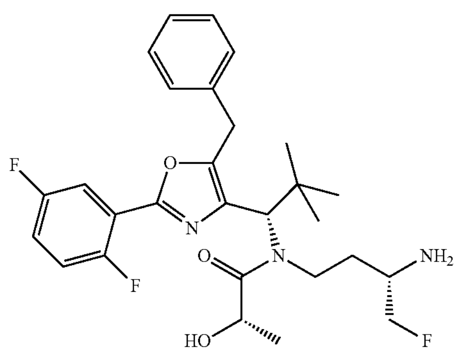 | 631 nM/N/A |
| 8 | 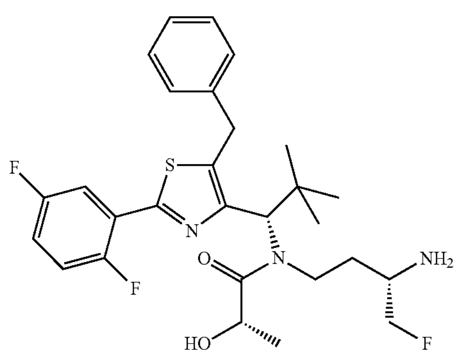 | 216 nM/944 nM |

Example 10

Inhibition of Cellular Proliferation in Tumor Cell Lines Treated with KSP Inhibitors Cells are plated in 96-well plates at densities of about 500 cells per well of a 96-well plate and are allowed to grow for 24 hours. The cells are then treated with various concentrations of compounds for 72 hours. Then, 100 µl of CellTiter-Glo® solution are added. The CellTiter-Glo® assay measures the amount of ATP present in the well after lysing the cells; the ATP released is used in an enzymatic reaction including the enzyme Luciferease and its substrate Luciferin. The amount of light emitted is proportional to the amount of ATP, which in turn is proportional to the number of live cells in the well. (see Promega product catalog #G7573, CellTiter-Glo® Luminescent Cell Viability Assay). The cells are then incubated in the dark for 30 minutes. The amount of luminescence is determined for each well using a Wallac Trilux plate reader, which correlates with the number of cells per well. The number of viable cells in the wells that receive only DMSO (0.5%) serve as an indication of 0°/a inhibition, while wells without cells serve as 100% inhibition of cell growth. The compound concentration that results in a 50% growth inhibition ($GI_{50}$) is determined graphically from sigmoidal dose-response curves of log-transformed dose values versus cell counts (percent of control) at 72 hours of continuous compound exposure.

The cell lines used are listed below.

The cell proliferation assay is performed as described above.

Cancer Cell Lines
Colo 205—colon carcinoma
  RPMI 1640+10% FBS+1% L-glutamine+1% P/S+1% NaPyr.+Hepes+4.5 g/L Glucose+1% NaBicarb.
MDA 435—breast cancer—high met
  EMEM+10% FBS+1% P/S+1% L-Glutamine+1% NEAA+1% NaPyr+1% vitamins
HCT-15 and HCT116—colon carcinoma
  RPMI 1640+10% FBS+1% L-glutamine+1% P/S
Drug Resistant Cell Lines
KB3.1—colon epidermal carcinoma; parental cell line
  Iscove's+10% FBS+1% L-glutamine+1% P/S
KBV1—p-glycoprotein associated multi-drug resistant cell line
  RPMI 1640+10% FBS+1% L-glutamine+1% P/S+0.2 ug/mL Vinblastine
KB85—p-glycoprotein associated multi-drug resistant cell line
  DMEM+10% FBS+1% L-glutamine+1% P/S+10 ng/mL Colchicine Preferred compounds of the invention have a biological activity as measured by an GI50 of less than about 1 mM in assay protocols described with some embodiments having biological activity of less than about 25 µM, with other embodiments having biological activity of less than about 1000 nM, and with still other embodiment having a GI50 of less than about 100 nM.

Example 11

Clonogenic Softagar Assay Protocol

Human cancer cells are plated at a density of $3\times10^5$ cells per well in a 6-well plate. The next day, a compound of interest at a certain concentration is added to each well. After 24 and 48 hours of incubation, the cells are harvested, washed and counted. The following steps are performed using the Multimek 96 robot. Then, 500 viable cells per well are plated in a 96-well plate that is coated with PolyHema to prevent attachment of the cells to the bottom of the well. Agarose (3% stock) is melted, diluted in warmed media and added to the cells to a final concentration of 0.5%. After the soft agar solidified, the plates are incubated at 37° C. for 6 days. Alamar blue dye is added to cells and plates are incubated for an additional 6 hours. The optical density change is measured on a Tecan plate reader and is considered to correlate with the number of colonies formed in soft agar. A cancerous cell is able to grow on the agar and thus will show an increase in optical density. A reading of decreased optical density means that the cancer cells are being inhibited. It is contemplated that compounds of this invention will exhibit a decrease in optical density.

What is claimed is:

1. A compound of Formula (I) or a pharmaceutically acceptable salt thereof:

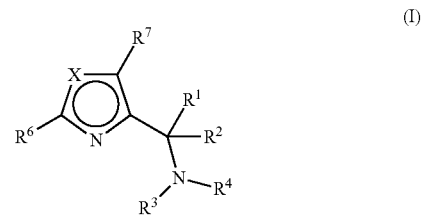

wherein:
$R^1$ is selected from the group consisting of alkyl, branched alkyl, and substituted alkyl;
$R^2$ is selected from the group consisting of hydrogen, alkyl, and substituted alkyl;
$R^3$ is selected from the group consisting of -$L_1$-$A^1$, wherein $L^1$ is selected from the group consisting of —C(O)—, —C(S)—, —S(O)—, and —S(O)$_2$— and $A^1$ is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, substituted heterocycloalkyl, and $NR^8R^9$;
$R^4$ is selected from the group consisting of hydrogen, alkyl, substituted alkyl, alkenyl, substituted alkenyl, alkynyl, and substituted alkynyl, and optionally substituted pyrrolidinyl;
X is O or S;
$R^6$ is selected from the group consisting of cycloalkyl, heterocycloalkyl, aryl, and heteroaryl, all of which may be optionally substituted with —$(R^{10})_m$ where $R^{10}$ is as defined herein, m is 1, 2, 3, or 4, and each $R^{10}$ may be the same or different when m is 2, 3, or 4;
$R^7$ is -$L^2$-$A^2$ wherein $L^2$ is $C_1$-$C_5$ alkylene and $A^2$ is selected from the group consisting of aryl, substituted aryl, heteroaryl, substituted heteroaryl, cycloalkyl, substituted cycloalkyl, heterocycloalkyl, and substituted heterocycloalkyl;
$R^8$ is selected from the group consisting of hydrogen and alkyl;
$R^9$ is selected from the group consisting of hydrogen, hydroxy, alkyl, substituted alkyl, aryl, substituted aryl, heteroaryl, substituted heteroaryl, cycloalkyl, substituted cycloalkyl, heterocycloalkyl, and substituted heterocycloalkyl;

or R⁸ and R⁹ together with the nitrogen atom pendent thereto join to form a heterocycloalkyl or substituted heterocycloalkyl;

R¹⁰ is selected from the group consisting of cyano, alkyl, substituted alkyl, alkenyl, substituted alkenyl, alkynyl, substituted alkynyl, —CF₃, alkoxy, substituted alkoxy, halo, and hydroxy; and R¹¹ is selected from the group consisting of hydrogen, alkyl, substituted alkyl, —SO₂alkyl, and —SO₂substituted alkyl.

2. A compound of claim 1, wherein R¹ is alkyl.

3. A compound of claim 1, wherein R² is C₁₋₄ alkyl or H.

4. A compound of claim 3, wherein R² is H.

5. A compound of claim 4, wherein R¹ is i-propyl, or t-butyl.

6. A compound of claim 5, wherein R³ is selected from -L¹-A¹, wherein L¹ is selected from the group consisting of —C(O)—, —C(S)—, —S(O)—, and —S(O)₂— and A¹ is selected from the group consisting of alkyl, and substituted alkyl.

7. A compound of claim 6, wherein R³ is selected from -L¹-A¹, wherein L¹ is —C(O)—, and A¹ is substituted alkyl.

8. A compound of claim 7, wherein R⁴ is selected from the group consisting of hydrogen, alkyl, and substituted alkyl.

9. A compound of claim 8, wherein R⁴ is substituted alkyl or —CH₂-fluoropyrrolidinyl.

10. A compound of claim 9, wherein R³ is selected from -L¹-A¹, wherein L¹ is —C(O)—, and A¹ is —CH(CH₃)OH.

11. A compound of claim 10, wherein R⁴ is —(CH₂)₂—CH(CH₂F)NH₂, or —CH₂-3-fluoropyrrolidinyl.

12. A compound of claim 11, wherein R⁶ is selected from the group consisting of aryl, and heteroaryl, all of which are optionally substituted with —(R¹⁰)ₘ where m is 1, 2, 3, or 4, and each R¹⁰ may be the same or different when m is 2, 3, or 4; and R⁷ is -L²-A² wherein L² is C₁-C₂ alkylene and A² is selected from the group consisting of aryl, and heteroaryl.

13. A compound of claim 12, wherein R⁶ represents aryl substituted with two R¹⁰ groups.

14. A compound of claim 12, wherein R⁶ represents phenyl substituted with two fluorine atoms.

15. A compound of claim 13, wherein R⁷ represents —CH₂-aryl.

16. A compound of claim 14 wherein R⁷ represents —CH₂-phenyl.

17. A compound selected from

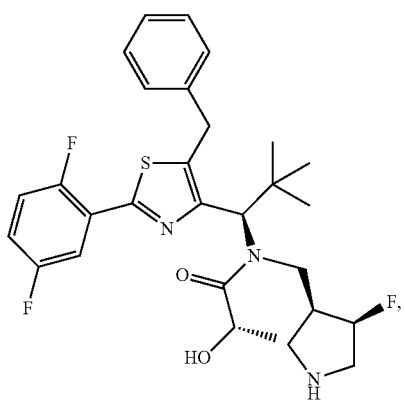

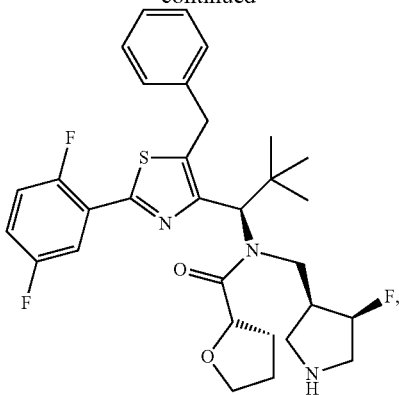

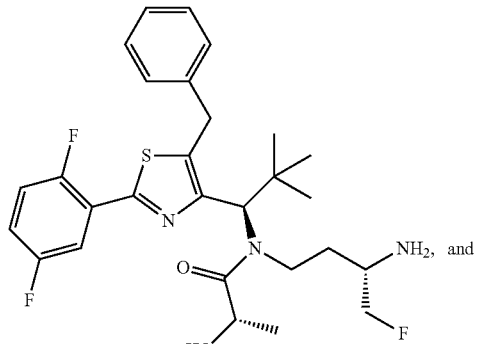

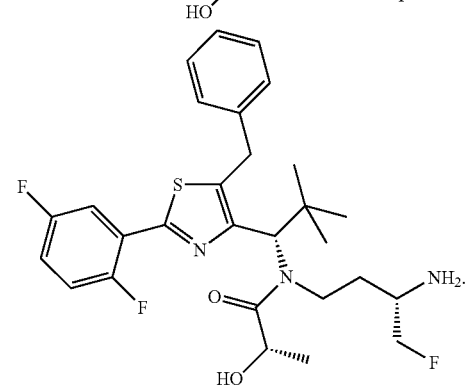

18. A pharmaceutical composition comprising a therapeutically effective amount of a compound of claim 1 and a pharmaceutically acceptable carrier.

19. The composition of claim 18 further comprising at least one additional agent for the treatment of cancer.

20. The composition of claim 19, wherein the additional agent for the treatment of cancer is selected from the group consisting of irinotecan, topotecan, gemcitabine, imatinib, 5-fluorouracil, leucovorin, carboplatin, cisplatin, docetaxel, paclitaxel, tezacitabine, cyclophosphamide, vinca alkaloids, anthracyclines, rituximab, and trastuzumab.

21. A method of treating a colon cancer or breast cancer mediated, at least in part, by kinesin spindle protein (KSP) in a mammalian patient in need of such treatment comprising administering to the mammalian patient a therapeutically effective amount of a compound of claim 1.

22. A method for inhibiting KSP in a mammalian patient, wherein said method comprises administering to the patient an effective KSP-inhibiting amount of a compound of claim 1.

23. A compound of claim 1 selected from:
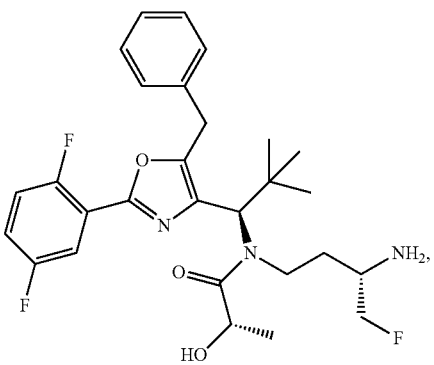
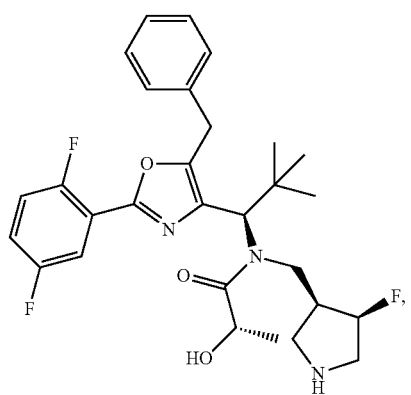
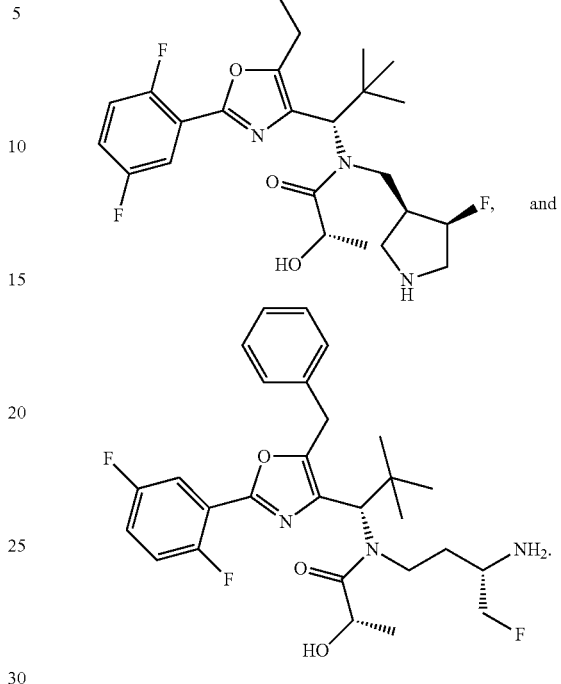
24. A method of treating a colon cancer or breast cancer mediated, at least in part, by KSP in a mammalian patient in need of such treatment, comprising administering to the mammalian patient a therapeutically effective amount of the pharmaceutical composition of claim 18.
* * * * *